US012629330B2

(12) United States Patent
Jang et al.

(10) Patent No.: US 12,629,330 B2
(45) Date of Patent: May 19, 2026

(54) POLYMER CARBON NITRIDE, SPECIFIC CRYSTAL FORM OF SAID POLYMER CARBON NITRIDE, AND ULTRAVIOLET RAY-BLOCKING USE THEREOF

(71) Applicant: UNIST(ULSAN NATIONAL INSTITUTE OF SCIENCE AND TECHNOLOGY), Ulsan (KR)

(72) Inventors: Ji Wook Jang, Ulsan (KR); Jae Sung Lee, Ulsan (KR); Woo Jin Byun, Ulsan (KR)

(73) Assignee: UNIST(ULSAN NATIONAL INSTITUTE OF SCIENCE AND TECHNOLOGY), Ulsan (KR)

( * ) Notice: Subject to any disclaimer, the term of this patent is extended or adjusted under 35 U.S.C. 154(b) by 479 days.

(21) Appl. No.: 18/255,536

(22) PCT Filed: Dec. 6, 2021

(86) PCT No.: PCT/KR2021/018367

§ 371 (c)(1),
(2) Date: Jun. 1, 2023

(87) PCT Pub. No.: WO2022/119420

PCT Pub. Date: Jun. 9, 2022

(65) Prior Publication Data

US 2024/0024222 A1 Jan. 25, 2024

(30) Foreign Application Priority Data

Dec. 4, 2020 (KR) ........................ 10-2020-0168537
Dec. 4, 2020 (KR) ........................ 10-2020-0168538

(51) Int. Cl.

*A61K 8/84* (2006.01)
*A61Q 17/04* (2006.01)
*C08G 73/08* (2006.01)

(52) U.S. Cl.

CPC ................ *A61K 8/84* (2013.01); *A61Q 17/04* (2013.01); *C08G 73/08* (2013.01)

(58) Field of Classification Search

None
See application file for complete search history.

(56) References Cited

U.S. PATENT DOCUMENTS

| | | | |
|---|---|---|---|
| 9,656,103 | B2 | 5/2017 | Müller et al. |
| 2008/0075746 | A1 | 3/2008 | Muller et al. |

FOREIGN PATENT DOCUMENTS

| | | | |
|---|---|---|---|
| CN | 110240191 | A | 9/2019 |
| JP | 2015-183011 | A | 10/2015 |
| JP | 2017-214235 | A | 12/2017 |
| KR | 10-1181362 | B1 | 9/2012 |

OTHER PUBLICATIONS

Dong et al., "Enhanced Visible Light Photocatalytic Activity and Oxidation Ability of Porous Graphene-like g-$C_3N_4$ Nanosheets via Thermal Exfoliation," *Applied Surface Science*, Dec. 2015, 358(A):393-403, article in press, 11 pages.

Hsu et al., "Fabrication and Photocatalytic Application of Aromatic Ring Functionalized Melem Oligomers," *J. Phys. Chem. C*, Jan. 27, 2018, 122:3506-3512.

International Search Report and Written Opinion, dated Mar. 14, 2022, issued in corresponding Application No. PCT/KR2021/018367, and English language translation of the International Search Report, 13 pages.

Notice of Allowance (Written Decision on Registration), dated Sep. 30, 2022, issued in related Korea Application No. 10-2020-0168537, plus English translation of Notice of Allowance, 4 pages.

Notice of Allowance (Written Decision on Registration), dated May 31, 2023, issued in related Korea Application No. 10-2020-0168538, plus English translation of Notice of Allowance, 4 pages.

Office Action (Request for the Submission of an Opinion), dated Mar. 29, 2022, issued in related Korea Application No. 10-2020-0168537, plus English translation of Office Action, 11 pages.

Office Action (Request for the Submission of an Opinion), dated Nov. 21, 2022, issued in related Korea Application No. 10-2020-0168538, plus English translation of Office Action, 13 pages.

Singh et al., "Emergence of Heptazine-Based Graphitic Carbon Nitride within Hydrogel Nanocomposites for Scarless Healing of Burn Wounds," *ACS Appl. Polym. Mater.*, Nov. 23, 2020, 2:5743-5755.

(Continued)

*Primary Examiner* — Nannette Holloman
(74) *Attorney, Agent, or Firm* — Klarquist Sparkman, LLP

(57) ABSTRACT

The present invention relates to a polymer carbon nitride, a specific crystal form of the polymer carbon nitride, and a cosmetic composition, an ultraviolet ray-blocking composition, and an external use skin preparation composition, which include the polymer carbon nitride. The polymer carbon nitride according to one aspect of the present invention and a crystal form produced by a specific preparation example thereof can absorb both UVA and UVB, and thus can effectively protect the skin from ultraviolet rays while also being non-toxic and thus suitable for living bodies and lacking photoactivity. Therefore, the polymer carbon nitride and the crystal form can be utilized in a cosmetic composition, an ultraviolet ray-blocking composition and an external use skin preparation composition, which are applied to the living body. Moreover, the specific crystal forms of the polymer carbon nitride have different characteristics according to the manufacturing method, and thus may be used in a variety of ways according to the characteristics. Particularly, the crystal form of the polymer carbon nitride according to one aspect can be adjusted to various colors according to the preparation method, and thus can be utilized to obtain a composition having a desired color. Therefore, the crystal form can be suitably utilized to produce products of various colors suitable for the skin tones of individuals.

13 Claims, 24 Drawing Sheets

(56) References Cited

OTHER PUBLICATIONS

Yang et al., Two-Photon Absorption in a Defect-Engineered Carbon Nitride Polymer Drives Red-Light Photocatalysis, *ChemCatChem*, 10.1002/cctc.202000803, published May 12, 2020, accepted manuscript, 13 pages.

Yuan et al., "UV Protection of Wood Surfaces by Graphitic Carbon Nitride Nanosheets," *Applied Surface Science*, published Oct. 30, 2018, 467:1070-1075, accepted manuscript, 16 pages.

Yuan et al., "UV Protection of Wood Surfaces by Graphitic Carbon Nitride Nanosheets," *Applied Surface Science*, Oct. 30, 2018, 467-468:1070-1075. 6 pages.

Liu Qiong et al: "Efficient photoreforming of lignocellulose into $H_2$ and photocatalytic $CO_2$ reduction via in-plane surface dyadic heterostructure of porous polymeric carbon nitride", Carbon, 2020, vol. 170, pp. 199-212 (Aug. 13, 2020).

Stagi Luigi et al: "Structural and optical properties of carbon nitride polymorphs", Diamond and Related Materials, 2016, vol. 68, pp. 84-92 (Jun. 18, 2016).

Sudhaik Anita et al: "Synergistic photocatalytic mitigation of imidacloprid pesticide and antibacterial activity using carbon nanotube decorated phosphorus doped graphitic carbon nitride photocatalyst" Journal of the Taiwan Institute of Chemical Engineers, 2020, vol. 113, pp. 142-154 (Aug. 1, 2020).

He Nannan et al: "Enhanced photocatalytic disinfection of *Escherichia coli* K-12 by porous g-$C_3N_4$ nanosheets: Combined effect of photogenerated and intracellular ROSs", Chemosphere, 2019, vol. 235, pp. 1116-1124 (Jul. 4, 2019).

Wu Shan et al: "A simple synthesis route of sodium-doped g-$C_3N_4$ nanotubes with enhanced photocatalytic performance", Journal of Photochemistry, 2021, vol. 406, 112999, (Nov. 2, 2020).

Prakash K et al: "Fruitful fabrication of CDs on GO/g-$C_3N_4$ sheets layers: A carbon amalgamation for the remediation of carcinogenic pollutants" Journal of Photochemistry, 2019, vol. 370, 94-104 (Oct. 25, 2018).

Chinese Patent Application No. 202180081947.8 First Office Action, mailed Jul. 1, 2025, 16 pages.

Mo, et al., "Effects of Different Precursors on Microstructure and Photocatalytic Properties of g—$C_3N_4$", *Journal of Guandong University of Petrochemical Technology*, 29(1):23-27 (Feb. 2019).

Office Action for Chinese Patent Application No. 202180081947.8, mailed Mar. 17, 2026.

Rhodamine B

FIG. 14

| No. | Initial | PRODUCT NAME | 4 | |
|---|---|---|---|---|
| | | 30 MINUTES AFTER | 24 HOURS AFTER | 48 HOURS AFTER |
| 1 | KJI | – | – | – |
| 2 | JJI | – | – | – |
| 3 | YJS | – | – | – |
| 4 | LJY | – | – | – |
| 5 | MKH | – | – | – |
| 6 | KYO | – | – | – |
| 7 | GJS | – | – | – |
| 8 | HM | – | – | – |
| 9 | HYJ | – | – | – |
| 10 | LBO | – | – | – |
| 11 | PMJ | – | – | – |
| 12 | RIS | – | – | – |
| 13 | KJS | – | – | – |
| 14 | KSJ | – | – | – |
| 15 | PJO | – | – | – |
| 16 | JHJ | – | – | – |
| 17 | CHJ | – | – | – |
| 18 | KJY | – | – | – |
| 19 | LMJ | – | – | – |
| 20 | JJH | – | – | – |
| 21 | LHN | – | – | – |
| 22 | LKS | – | – | – |
| 23 | JYJ | – | – | – |
| 24 | YHS | – | – | – |
| 25 | KAR | – | – | – |
| 26 | SYJ | – | – | – |
| 27 | GSH | – | – | – |
| 28 | KHS | – | – | – |
| 29 | JHJ-2 | – | – | – |
| 30 | YYM | – | – | – |
| REACTION RATE | ± | 0 | 0 | 0 |
| | + | 0 | 0 | 0 |
| | ++ | 0 | 0 | 0 |
| | +++ | 0 | 0 | 0 |
| Mean score : | | 0.00 | | |
| JUDGEMENT | | NON-IRRITATING | | |

POLYMER CARBON NITRIDE, SPECIFIC CRYSTAL FORM OF SAID POLYMER CARBON NITRIDE, AND ULTRAVIOLET RAY-BLOCKING USE THEREOF

CROSS REFERENCE TO RELATED APPLICATIONS

This is the U.S. National Stage of International Application No. PCT/KR2021/018367, filed Dec. 6, 2021, which claims the benefit of Korean Patent Application No. 10-2020-0168538 and Korean Patent Application No. 10-2020-0168537, filed with the Korean Intellectual Property Office on Dec. 4, 2020, the disclosures of which are incorporated in the present specification by reference.

TECHNICAL FIELD

The present disclosure relates to a polymeric carbon nitride, a specific crystal form of the polymeric carbon nitride, and ultraviolet ray-blocking use thereof.

BACKGROUND ART

Ultraviolet (UV) rays are solar radiation in the wavelength range of 280 to 400 nanometers, and exposure to excessive amounts of UV can cause skin damage, including skin aging, burns, and skin cancer. In particular, ultraviolet-A (UVA) in the 320 to 400 nanometer wavelength range is known to accelerate skin aging by damaging skin lipids in the epidermis and causing melanin pigmentation in the underlying layer. In addition, ultraviolet-B (UVB) in the wavelength range of 280 to 320 nanometers is known to directly damage the skin by causing skin erythema, skin burns, and the like. Therefore, the development of various materials to protect the skin from UV radiation by blocking UVA and UVB simultaneously is required.

In particular, excessive exposure to UV radiation can cause skin cancer, therefore there is a high need for UV-blocking agents to prevent life-threatening diseases and skin wrinkles. Two frequently used inorganic UV-blocking agents are zinc oxide (ZnO) and titanium dioxide ($TiO_2$), however the use of such inorganic UV-blocking agents poses serious health concerns. Such photoactive metal oxide semiconductor sunscreens produce hydroxyl radicals (·OH) and peroxyl radicals ($O_2$·−) in the process of absorbing UV. The generation of such highly reactive oxygen species (ROS) not only degrades the organic additives in UV-blocking agents, but also causes oxidative stress in skin tissue, which can cause damage at the cellular level and promote DNA modification and inflammatory responses. Therefore, research is ongoing to develop safe UV-blocking agents that can replace inorganic UV-blocking agents of zinc oxide (ZnO) and titanium dioxide ($TiO_2$) (Korean Publication Patent No. 10-2020-0047249).

Recently, studies have been attempted to remove carcinogenic ROS by wrapping inorganic and organic materials, but their potential has not been proven for commercialization. Therefore, there is a need for a material that absorbs light energy in the entire UV spectrum while solving such problems, is highly stable, has low photocatalytic activity, and is biocompatible and non-toxic.

DISCLOSURE

Technical Problem

An objective of the present disclosure is to provide a polymeric carbon nitride (PCN), a specific crystal form of the PCN, and an ultraviolet ray (UV)-blocking use thereof, in order to solve the problems.

One objective of the present disclosure is to provide a crystal form of PCN selected from the group consisting of crystal forms A to G.

Another objective of the present disclosure is to provide a cosmetic composition, a composition for UV-blocking, and an external use skin preparation composition including the PCN or the specific crystal form of the PCN.

Another objective of the present disclosure is to provide a method of producing a cosmetic composition, a composition for UV-blocking, or an external use skin preparation composition including the process of adding the PCN or the specific crystal form of the PCN Another objective of the present disclosure is to provide a UV-blocking use of the PCN, the specific crystal form of the PCN, or a composition including the PCN or the specific crystal form of the PCN.

However, the technical challenges of the present disclosure are not limited to challenges mentioned above, and other challenges not mentioned will be apparent to one of ordinary skill in the art from the following description.

Technical Solution

According to an embodiment of the present disclosure, provided is a crystal form of polymeric carbon nitride (PCN) selected from the group consisting of crystal forms A to G having the following X-ray powder diffraction pattern as measured using CuKα radiation, wherein the X-ray powder diffraction pattern of the crystal form A includes peaks at one or more diffraction angles selected from the group consisting of 2θ=10.7656±0.2°, 19.8006±0.2°, and 29.7456±0.2°, the X-ray powder diffraction pattern of the crystal form B includes peaks at one or more diffraction angles selected from the group consisting of 2θ=10.7396±0.2° and 29.7456±0.2°, the X-ray powder diffraction pattern of the crystal form C includes peaks at one or more diffraction angles selected from the group consisting of 2θ=10.7006±0.2°, 22.1406±0.2°, and 27.8606±0.2°, the X-ray powder diffraction pattern of the crystal form D includes peaks at one or more diffraction angles selected from the group consisting of 2θ=10.6356±0.2° and 27.8216±0.2°, the X-ray powder diffraction pattern of the crystal form E includes peaks at one or more diffraction angles selected from the group consisting of 2θ=10.7266±0.2° and 27.5096±0.2°, the X-ray powder diffraction pattern of the crystal form F includes a peak at a diffraction angle of 2θ=27.1586±0.2°, the X-ray powder diffraction pattern of the crystal form G includes peaks at one or more diffraction angles selected from the group consisting of 2θ=13.8076±0.2° and 27.1586±0.2°.

The "polymeric carbon nitride" may include repeating units represented by Formula 1.

[Formula 1]

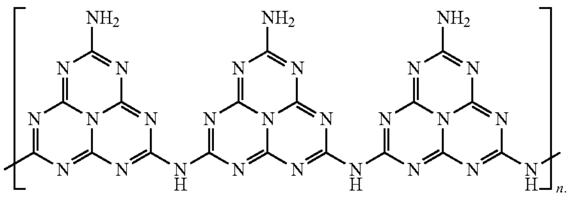

In Formula 1, n may be an integer, for example, an integer between 1 and 1,000,000. The PCN of Formula 1 may be a polymer having a molecular weight of, for example, about 200 amu to 5,000,000 amu, about 400 amu to 4,000,000 amu, about 600 amu to 3,000,000 amu, or about 800 amu to 2,000,000 amu.

The crystal form of the PCN of an aspect is a polymer that is thermally and chemically very stable, exhibits a white color to the naked eye, and has the characteristics of being easily dispersed when included in a composition. In one embodiment, it was confirmed that a new crystal form of the PCN has new properties and this was specified.

In an aspect, the PCN crystal forms A to G may have the following absorption peaks. Specifically, the PCN crystal forms A to G may have a characteristic (or property) selected from the group consisting of an infrared (IR) spectrum of the crystal form A including characteristic absorption peaks at 775±2 $cm^{-1}$, 1417 $cm^{-1}$, 1456 $cm^{-1}$, 1691 $cm^{-1}$, 1730 $cm^{-1}$, 3074 $cm^{-1}$, and 3311 $cm^{-1}$; an IR spectrum of the crystal form B including characteristic absorption peaks at 777±2 $cm^{-1}$, 1677±2 $cm^{-1}$, 1735±2 $cm^{-1}$, 3085±2 $cm^{-1}$, and 3315±2 $cm^{-1}$; an IR spectrum of the crystal form C including characteristic absorption peaks at 777±2 $cm^{-1}$, 1467±2 $cm^{-1}$, 1666±2 $cm^{-1}$, 1734±2 $cm^{-1}$, 3120±2 $cm^{-1}$, and 3320±2 $cm^{-1}$; an IR spectrum of the crystal form D including characteristic absorption peaks at 777±2 $cm^{-1}$, 1465±2 $cm^{-1}$, 1660±2 $cm^{-1}$, 1734±2 $cm^{-1}$, 3085±2 $cm^{-1}$, and 3330±2 $cm^{-1}$; an IR spectrum of the crystal form E including characteristic absorption peaks at 810±2 $cm^{-1}$, 1270±2 $cm^{-1}$, 1420±2 $cm^{-1}$, 1612±2 $cm^{-1}$, 3105±2 $cm^{-1}$, and 3330±2 $cm^{-1}$; an IR spectrum of the crystal form F including characteristic absorption peaks at 810±2 $cm^{-1}$, 1265±2 $cm^{-1}$, 1325±2 $cm^{-1}$, 1417±2 $cm^{-1}$, 1618±2 $cm^{-1}$, and 3230±2 $cm^{-1}$; and an IR spectrum of the crystal form G including characteristic absorption peaks at 810±2 $cm^{-1}$, 1240±2 $cm^{-1}$, 1317±2 $cm^{-1}$, 1410±2 $cm^{-1}$, 1560±2 $cm^{-1}$, 1635±2 $cm^{-1}$, and 3250±2 $cm^{-1}$.

In addition, the PCN crystal forms A to G may be one in which, upon X-ray photoelectron spectroscopy (XPS) analysis, a C (carbon) peak is present in the range of about 280 eV to 290 eV, an N (nitrogen) peak is present in the range of about 390 eV to 400 eV, and an O (oxygen) peak is present in the range of about 530 eV to 540 eV.

In addition, the crystal forms A to G can absorb ultraviolet (UV) rays from solar radiation with high absorption, for example ultraviolet-A (UVA) having a wavelength of about 320 nm to 400 nm and ultraviolet-B (UVB) having a wavelength of about 280 nm to 320 nm, thereby preventing skin damage caused by UV. Therefore, the PCN crystal forms of crystal forms A to G can strongly absorb light energy, for example, in the wavelength region of about 200 nm to 400 nm, about 220 nm to 400 nm, or about 280 nm to 400 nm.

The PCN crystal forms A to G may have an average particle diameter of, for example, about 1 nm to 10 nm, about 2 nm to 8 nm, about 3 nm to 6 nm, or about 4 nm to 5 nm. In an embodiment, the average particle diameter of PCN crystal forms A to G was confirmed by atomic force microscopy (AFM).

The PCN crystal forms A to G may include 2D nanosheets, and the thickness (height) of such nanosheets may be, for example, about 1 nm to 10 nm, about 2 nm to 8 nm, about 3 nm to 6 nm, or about 4 nm to 5 nm, and the thickness of such nanosheets may effectively cover the skin surface.

The color of the crystal form of the PCN can be adjusted and the crystal form of the PCN may be applicable based on skin tone. Since the crystal form of the PCN has a characteristic of being color adjustable depending on the method of production, when used, it can be adjusted to a desired color composition, making it suitable for producing products of various colors to suit individual skin tones.

The PCN crystal forms A to G may not exhibit cytotoxicity, and may not generate reactive oxygen species (ROS) when irradiated with UV.

According to another embodiment of the present disclosure, provided are a cosmetic composition, a composition for UV-blocking, and an external use skin preparation composition including a PCN including repeating units represented by Formula 1.

[Formula 1]

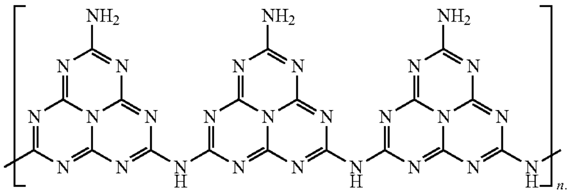

In Formula 1, n may be an integer, for example, an integer between 1 and 1,000,000. The PCN with Formula 1 may be a polymer having a molecular weight of, for example, about 200 amu to 5,000,000 amu, about 400 amu to 4,000,000 amu, about 600 amu to 3,000,000 amu, or about 800 amu to 2,000,000 amu.

The composition may include the PCN as an active ingredient.

The PCN included in the composition may include one or more crystal forms selected from the group consisting of the PCN crystal forms A to G.

The color of the PCN can be adjusted and the PCN may be applicable according to skin tone. Since the PCN has a characteristic of being color adjustable when produced by an appropriate method of production in the art, it can be adjusted and produced to a desired color when used to produce a cosmetic composition, a composition for UV-blocking, and an external use skin preparation composition.

In the specification, the term "cosmetic composition" refers to an article used on the human body to clean, beautify, and add attractiveness to the human body, to lighten appearance, or to maintain or promote the health of skin or hair. The cosmetic composition may be for UV-blocking.

The PCN may be included in an amount of about 0.001 wt % to 35 wt %, about wt % to 30 wt %, about 0.1 wt % to 30 wt %, about 0.1 wt % to 25 wt %, about 0.5 wt % to 35 wt %, about 0.5 wt % to 30 wt %, about 0.5 wt % to 25 wt %, about 0.5 wt % to 20 wt %, about 0.5 wt % to 15 wt %, about 0.5 wt % to 10 wt %, about 1 wt % to 35 wt %, about 1 wt % to 30 wt %, about 1 wt % to 25 wt %, about 1 wt % to 20 wt %, about 1 wt % to 15 wt %, about 1 wt % to 10 wt %, about 5 wt % to 35 wt %, about 5 wt % to 30 wt %, about 5 wt % to 25 wt %, about 5 wt % to 20 wt %, about 5 wt % to 15 wt %, about 5 wt % to 10 wt %, about 1 wt %, about 5 wt %, about 10 wt %, or about 15 wt %, based on the total weight of the composition. If the content of the PCN is lower than the content described above, the composition does not have a UV blocking effect, and if the content is higher than the content described above, the formulation stability may be significantly reduced in the composition.

In addition to the ingredients listed above, the composition may further include one or more selected from the group consisting of purified water, preservatives, stabilizers, surfactants, thickeners, solubilizers, moisturizer, emollients, UV absorbers, antiseptics, germicides, emulsifiers, antioxidants, pH adjusters, organic and inorganic pigments, fragrances, carrier, cooling agents, and restricting agents, and may further include, for example, additives commonly used in the art. The blending amount of additional ingredients, such as preservatives, may be readily selected by those skilled in the art without impairing the objective and effect of the present disclosure, and the blending amount may range from about 0.001 wt % to 30 wt % (w/w) based on the total weight of the composition, however, those skilled in the art may select any additional ingredients and/or amounts thereof such that the advantageous properties of the composition according to the present specification are not adversely affected or substantially not affected by the anticipated addition.

The composition may additionally include an organic UV-blocking agent and/or an inorganic UV-blocking agent, and may additionally include, for example, one or more selected from the group consisting of ethylhexylmethoxycinnamate, titanium dioxide, zinc oxide, butylmethoxydibenzoylmethane, isoamyl p-methoxycinnamate, ethylhexyl salicylate, octocrylene, homosalate, phenylbenzimidazole sulfonic acid, diethylaminohydroxybenzoylhexylbenzoate, ethylhexyltriazone, terephthalylidene dicamphorsulfonic acid, polysilicon-15, avobenzone, and oxybenzone. The additional UV-blocking agent may be included in about 1 wt % to 50 wt %, about 5 wt % to 45 wt %, about wt % to 40 wt %, about 5 wt % to 30 wt %, about 5 wt % to 20 wt %, about 5 wt % to 10 wt %, about 10 wt % to 30 wt %, or about 15 wt % to 25 wt %, based on the total weight of the composition.

The composition of an aspect may provide synergistic effects on UV-blocking when further including or combining additional organic UV-blocking agent and/or inorganic UV-blocking agent. In the present specification, the term "combination" refers to the simultaneous inclusion of the PCN and an additional organic UV-blocking agent and/or inorganic UV-blocking agent in the composition.

The PCN or the PCN crystal forms A to G included in the composition can absorb UV in solar radiation with high absorption, and can strongly absorb light energy in the wavelength region of about 200 nm to 400 nm, for example, UVA with a wavelength of about 320 nm to 400 nm and UVB with a wavelength of about 280 nm to 320 nm, thereby preventing skin damage caused by UV. Therefore, the composition including the PCN or the PCN crystal forms A to G may absorb light energy in the wavelength region of about 200 nm to 400 nm, about 220 nm to 400 nm, or about 280 nm to 400 nm. Specifically, the composition may absorb UVA having a wavelength of about 320 nm to 400 nm and UVB having a wavelength of about 280 nm to 320 nm.

The composition may be produced in formulations such as cosmetic water (skin lotion), skin softener, skin toner, astringent, lotion, milk lotion, moisturizing lotion, nourishing lotion, massage cream, cream, sunscreen, nourishing cream, moisturizing cream, hand cream, foundation, essence, nourishing essence, pack, soap, cleansing foam, cleansing lotion, cleansing cream, body lotion, body cleanser, suspension, gel, powder, paste, pact, facial mask or sheet mask, or aerosol, etc. The composition of such formulations may be produced according to methods common in the art.

The external use skin preparation may be a cream, gel, ointment, emollient, skin suspension, transdermal patch, drug-containing bandage, lotion, or a combination thereof. The external use skin preparation may be appropriately formulated according to need with ingredients commonly used in external use skin preparations such as cosmetics or pharmaceuticals, for example, water-based ingredients, oil-based ingredients, powder ingredients, alcohols, moisturizer, thickeners, UV absorbers, whitening agents, antiseptics, antioxidants, surfactants, fragrances, color agents, various skin nutrients, or combinations thereof. The external use skin preparation may appropriately formulate metal adhesives such as sodium edetate, trisodium edetate, sodium citrate, sodium polyphosphate, sodium metaphosphate, gluconic acid, etc., drugs such as caffeine, tannins, bellapamil, licorice extract, glabridin, hydrothermal extract of Carlin's fruit, various herbal medicines, acetic acid tocopherol, glycyrrhizic acid, tranexamic acid and derivatives thereof or salts thereof, etc., sugars such as vitamin C, magnesium ascorbate phosphate, ascorbic acid glucoside, arbutin, kojic acid, glucose, fructose, trehalose, etc.

The skin includes all skin areas of the body, including the face, hands, arms, legs, feet, chest, stomach, back, buttocks, and scalp.

The composition of an aspect can be applied, administered, and rubbed to an individual. The term "individual" includes any mammal, such as a human or non-human primate, mouse, dog, cat, horse, and bovine, etc.

Among the terms or elements mentioned in the composition, the same as those mentioned in the description of the crystal form are understood to be the same as those mentioned in the previous description of the crystal form above.

According to another embodiment of the present disclosure, provided is a method of producing a cosmetic composition, a composition for UV-blocking, or an external use skin preparation composition including the process of adding a PCN including repeating units represented by Formula 1.

[Formula 1]

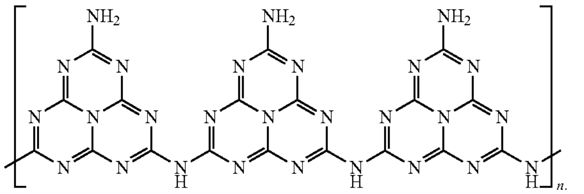

In Formula 1, n may be an integer, for example, an integer between 1 and 1,000,000. The PCN with Formula 1 may be a polymer having a molecular weight of, for example, about 200 amu to 5,000,000 amu, about 400 amu to 4,000,000 amu, about 600 amu to 3,000,000 amu, or about 800 amu to 2,000,000 amu.

The PCN may include one or more crystal forms selected from the group consisting of the PCN crystal forms A to G.

Among the terms or elements mentioned in the method, the same as those mentioned in the description of the crystal form and composition are understood to be the same as those mentioned in the previous description of the crystal form and composition above.

According to another embodiment of the present disclosure, a UV-blocking use of a PCN including repeating units represented by Formula 1, or a composition including the PCN, is provided.

[Formula 1]

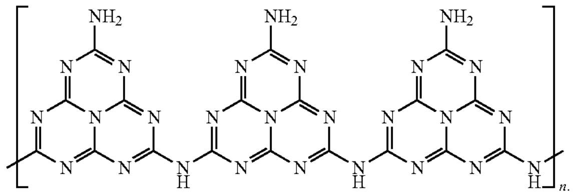

In Formula 1, n may be an integer, for example, an integer between 1 and 1,000,000. The PCN with Formula 1 may be a polymer having a molecular weight of, for example, about 200 amu to 5,000,000 amu, about 400 amu to 4,000,000 amu, about 600 amu to 3,000,000 amu, or about 800 amu to 2,000,000 amu.

The PCN may include one or more crystal forms selected from the group consisting of the PCN crystal forms A to G.

Among the terms or elements mentioned in the usage, the same as those mentioned in the description of the crystal form, composition, and method are understood to be the same as those mentioned in the previous description of the crystal form, composition, and method above.

Advantageous Effects

Polymer carbon nitride (PCN) of an aspect and a crystal form produced by specific a preparation example thereof can absorb both ultraviolet-A (UVA) and ultraviolet-B (UVB), therefore effectively protecting the skin from ultraviolet (UV) rays, while being non-toxic, biocompatible, and non-photoactive, and may be used in a cosmetic composition, a composition for UV-blocking, and an external use skin preparation composition applied to the body. In addition, the specific crystal form of the PCN has different characteristics depending on the method of production, so it may be used in various ways according to its properties. In particular, since the crystal form of the PCN of an aspect has a characteristic that can be adjusted to various colors depending on the method of production, when used, it can be adjusted to a desired color composition, making it suitable for producing products of various colors to suit individual skin tones.

DESCRIPTION OF DRAWINGS

FIG. 14 shows the results of evaluating skin irritation by patch test of CN-400-4 on subjects.

MODE FOR INVENTION

Figure 1A:
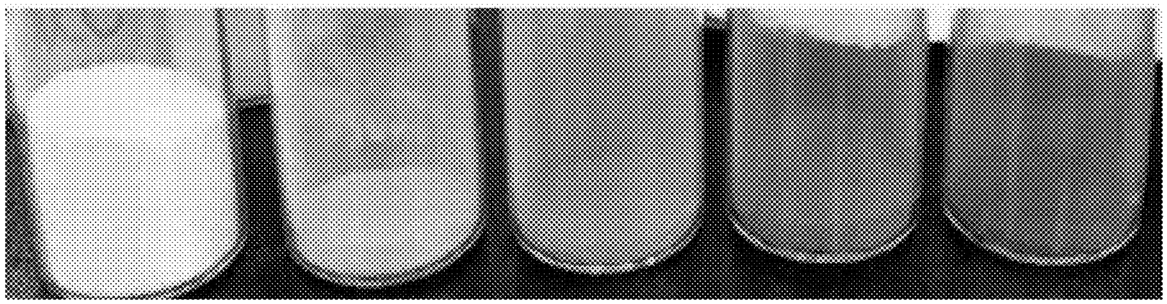
FIG. 1A is a schematic view showing that when a polymeric carbon nitride (PCN) is produced by a method of production described in one aspect, it is possible to produce a crystal form of various colors as well as white.

The respective characteristics of the many experimental examples and examples of the present disclosure may be combined or assembled with each other in part or in whole, and as will be fully appreciated by those skilled in the art, various interlocking and operational arrangements are technically possible, and each experimental example and example can be independently performed or can be performed in association with each other.

In interpreting the components, they are to be construed to include a margin of error, even if not expressly stated otherwise.

The shapes, sizes, proportions, angles, numbers, etc. disclosed in the drawings for explaining the experimental examples and examples of the present disclosure are exemplary and do not limit the present disclosure to those shown. In addition, in describing the present disclosure, detailed descriptions of related prior art are omitted in the case it is confirmed that such detailed descriptions may unnecessarily obscure the essence of the present disclosure. In the present specification, in cases where terms such as “comprises”, “includes”, “consists of”, etc. are used, other elements may be added unless the term “only” is used. In cases where the components are expressed in the singular form, they include the plural form unless otherwise expressly stated.

It will be described in more detail by the following experimental examples and examples. However, such experimental examples and examples are intended to exemplify one or more specific examples and the scope of the present disclosure is not limited to such experimental examples and examples.

Example 1. Confirmation of Experimental Materials $TiO_2$ (P-25, Degussa) was purchased from Degussa and ZnO was purchased from Alfa-Aesar. The organic ultraviolet ray (UV) filter ingredients avobenzone (catalog number PHR 1073) and oxybenzone (catalog number H36206) for UV-blocking agents were purchased from Sigma-Aldrich (USA).

Moisturizing cream was purchased from *Nivea* and sunscreen lait solaire hydratant SPF 15 was purchased from Viodem.

Dulbecco’s Modified Eagle’s Medium (DMEM), phosphate buffered saline (PBS) 1xpH 7.4 solution, bovine fetal serum (FBS), penicillin/streptomycin, and live/dead analysis for NIH-3T3 cell culture were purchased from Gibco by Life technologies. Dihydroxyethidium (DHE) and neutral buffered formalin solution (NBF solution, 10%) were purchased from Sigma Aldrich, USA. 3-(4,5-Dimethylthiazol-2-yl)-2,5-diphenyltetrazolium bromide (MTT) was purchased from ACROS Organics. Mitotracker deep red was purchased from Thermo fisher, USA. Artificial skin was purchased from Micropig® Franz Cell Membrane (FCM) of APURES Co. Ltd, Korea.

Example 2. Synthesis of Polymeric Carbon Nitride (PCN)

Figure 1B:
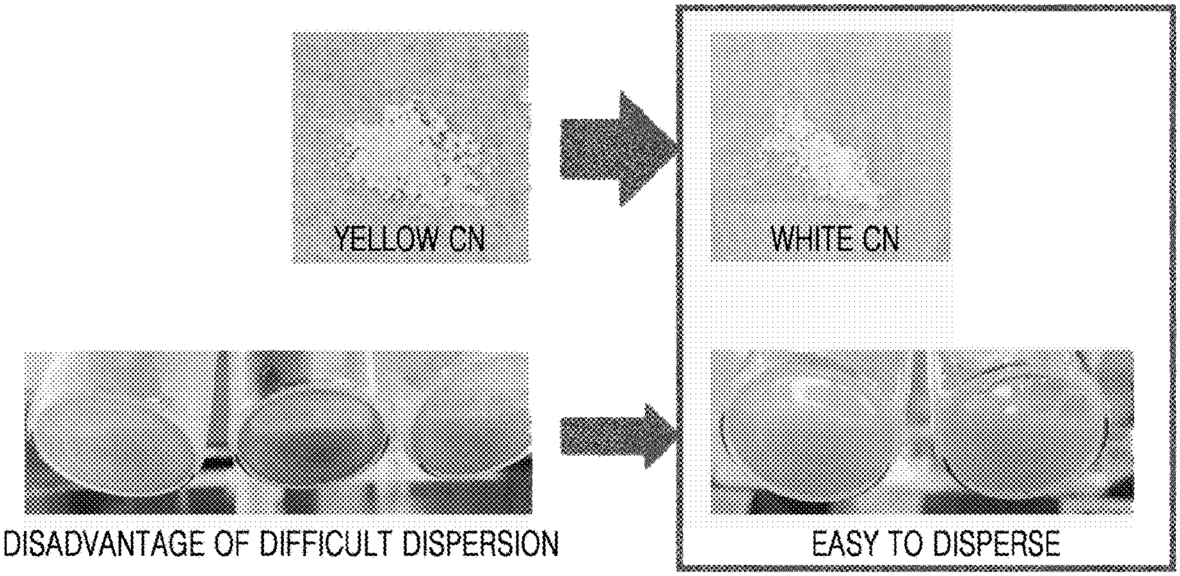
FIG. 1B is a schematic view confirming the difference in color and the difference in the degree of dispersion in a water-soluble solvent, between a yellow conventional PCN, which is difficult to disperse, and a white PCN, which is well dispersed, produced by the method of production described in one aspect.

The PCN used in this example was prepared by heat-treating urea having a concentration of 99% purchased from Aldrich, under ambient pressure. Melamine, dicyandiamide, cyanamide, or urea were used as precursors, and the precursor was placed in a heating furnace (Chamber Furnace UAF, Lenton) and heated at a temperature of 450° C. to 550° C. for 0.5 hours to 8 hours in a muffle furnace (Chamber Furnace UAF, Lenton) to complete the polycondensation reaction. The reaction product was washed with deionized water to remove residual species, and then dried at 80° C. overnight to produce the PCN used in the following example. The finally confirmed PCNs produced by the method of an aspect described above are shown in FIG. 1A and FIG. 1B. As shown in FIG. 1A, in the case of the crystal form produced by the method of an aspect, various colors could be produced by changing the temperature conditions during the production process or adding additives during the production process. In addition, as confirmed in FIG. 1B, when produced by the method of an aspect compared to a conventional method (for example, for CN-350-2, CN-400-0.5, CN-400-1, CN-400-2, CN-400-4, and CN-400-8 which are polycondensed PCNs at about 300° C. to 500° C. for about 0.3 hours to 10 hours), it was confirmed that a white PCN could be produced unlike a conventional yellow PCN, and thus it was confirmed that the white PCN produced was better dispersed in an water-soluble solvent compared to the conventional yellow PCN. Hereinafter, an experiment was conducted to confirm the properties of the PCN produced in this example.

Example 3. Crystallization-Centered Confirmation of Physical Properties of PCN 3.1 Confirmation of Properties of PCN by X-Ray Photoelectron Spectroscopy (XPS)

Figure 2A:
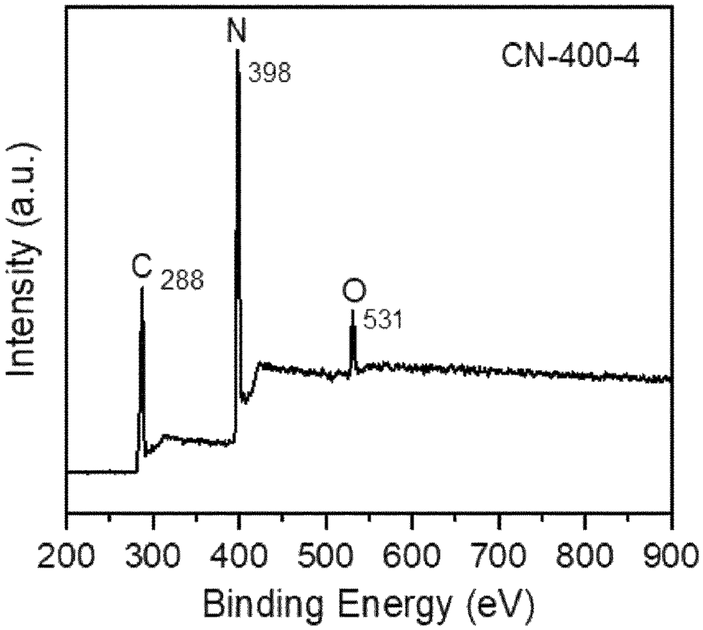
FIG. 2A is a schematic view showing a spectrum confirmed by X-ray photoelectron spectroscopy (XPS) for a CN-400-4 sample.
Figure 2B:
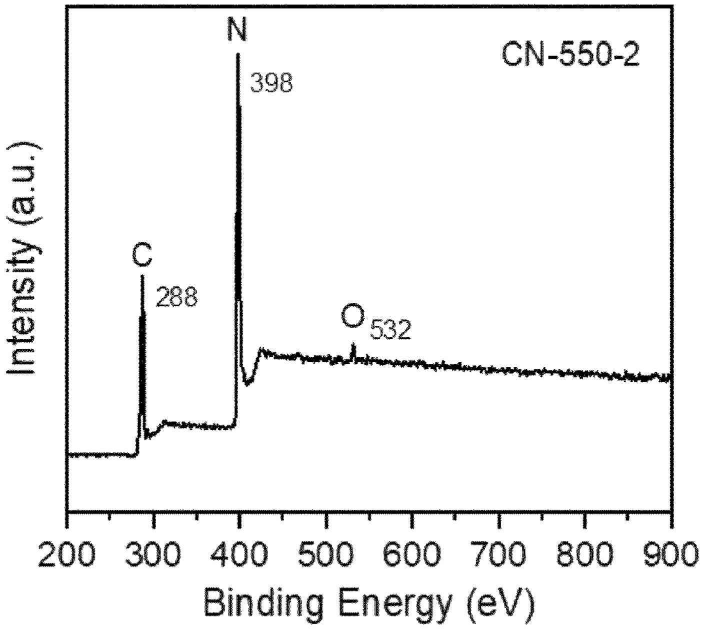
FIG. 2B is a schematic view showing a spectrum confirmed by XPS for a CN-550-2 sample.

The structure of the produced PCN was confirmed by XPS. Spectrum for CN-400-4 sample and CN-550-2 sample are shown in FIG. 2A and FIG. 2B. From the data of FIG. 2A and FIG. 2B, the relative atomic percentages of the elements C, N, and O on the sample surface were calculated accordingly. As confirmed in FIG. 2A and FIG. 2B, it was confirmed by scan spectrum that both samples include carbon, nitrogen, and oxygen. In CN-400-4, it was confirmed that peaks appeared at 288 eV for C, 398 eV for N, and 531 eV for O. In CN-550-2, it was confirmed that peaks appeared at 288 eV for C, 398 eV for N, and 532 eV for O. In addition, it was confirmed that the small oxygen peak of the CN-550-2 sample was caused by a small amount of partially polymerized urea present in this sample. In contrast, a significantly high concentration of oxygen was observed in the XPS spectrum of CN-400-4, and it was confirmed that the high concentration of oxygen was due to chemically bonded oxygen species in partially polymerized urea.

3.2 Confirmation of Properties of PCN by X-Ray Diffraction Analysis (XRD)

Various PCNs with various physical, chemical, optical and electronic structural properties were produced by thermal condensation of urea in air under different polymerization conditions. Since the produced polymerized carbon nitride had a triazine-based crystal structure, the final product could be described by properties as PCN. X-ray diffraction (XRD) patterns were collected with an X-ray diffractometer (X'Pert PRO MPD, PANalytical) using monochromated Cu Kα (I=0.1541 nm) radiation at 40 kV and 30 mA.

The crystal structures of the PCN samples produced by the polycondensation process at various temperatures under atmospheric pressure were analyzed by X-ray diffraction analysis (XRD). The results of confirming XRD of the produced PCN samples, CN-400-4 and CN-550-2, selected for UV-blocking applications, are shown in FIG. 3A, the results of confirming XRD patterns of other produced PCN samples, CN-350-2, CN-400-0.5, CN-400-1, CN-400-2, and CN-400-8, as well as the XRD of CN-400-4 and CN-550-2, are shown in FIG. 3B, the result of confirming the XRD of the PCN produced at a polymerization temperature of 400° C. are shown in FIG. 3C.

Figure 3A:
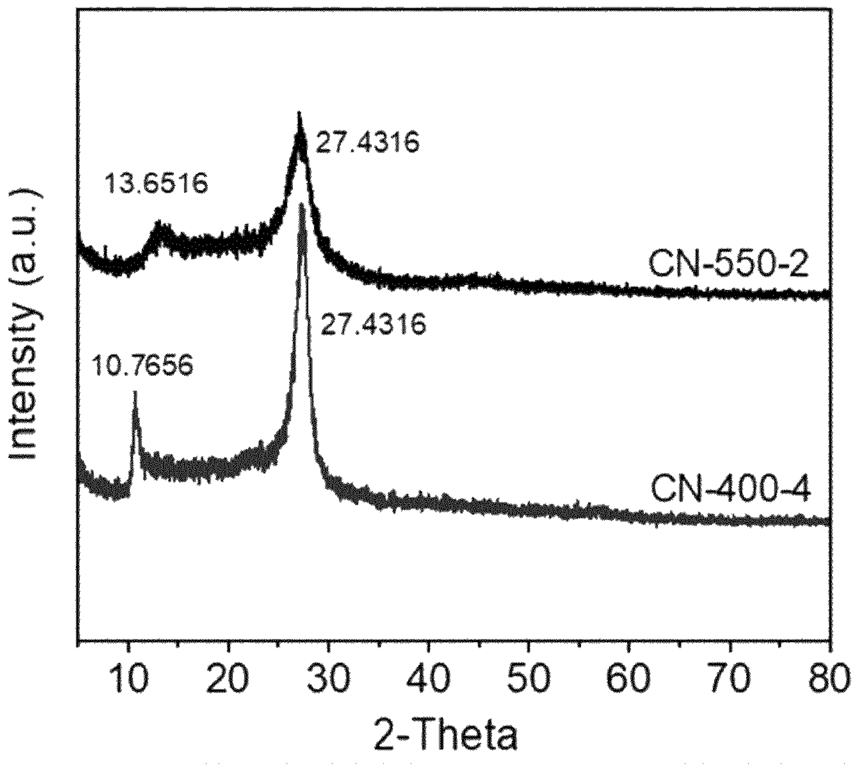
FIG. 3A shows the results of X-ray diffraction analysis (XRD) of CN-400-4 and CN-550-2 selected for UV-blocking applications.

As confirmed in FIG. 3A, it was confirmed that CN-400-4 a PCN polycondensed at 400° C. for 4 hours, showed two distinct diffraction peaks at 10.7656° and 27.4316° without any other impurity phase. In addition, it was able to confirm that the XRD pattern of CN-550-2 a PCN produced by polycondensation at 550° C. for 2 hours, showed two distinct diffraction peaks at 13.6516° and 27.4316° without any other impurity phase. It was confirmed that the XRD pattern of CN-550-2 sample was confirmed to be similar to bulk graphitic carbon nitride (g-C3N4) with a strong peak at 27.4° in the (002) plane, which was due to the interlayer stacking of condensed aromatic segments with 0.326 nm d-spacing. It was confirmed that the produced PCN exhibit structural stability, by this interlayer stacking the CN-550-2 sample similar to crystal graphite (d=0.335 nm) and tighter than the packing of carbon with graphene units (d=0.353 nm). It was confirmed that the weak peak at 13.6516° of the (100) plane corresponds to a planar structural packing motif with a repeated unit of 0.618 nm for the CN-550-2 sample, but is missing from the XRD patterns of CN-400-4 and other produced PCNs. It was confirmed to be due to incomplete or partial polycondensation of the urea at calcination temperatures of 400° C. or less. It was confirmed by evaluation of the XRD crystal structure results that the urea included in the CN-400-4 sample and CN-550-2 sample were partially and completely transformed to bulk g-C3N4, respectively. It was confirmed that this was mainly due to complete thermal condensation of the urea at higher temperatures.

Figure 3B:
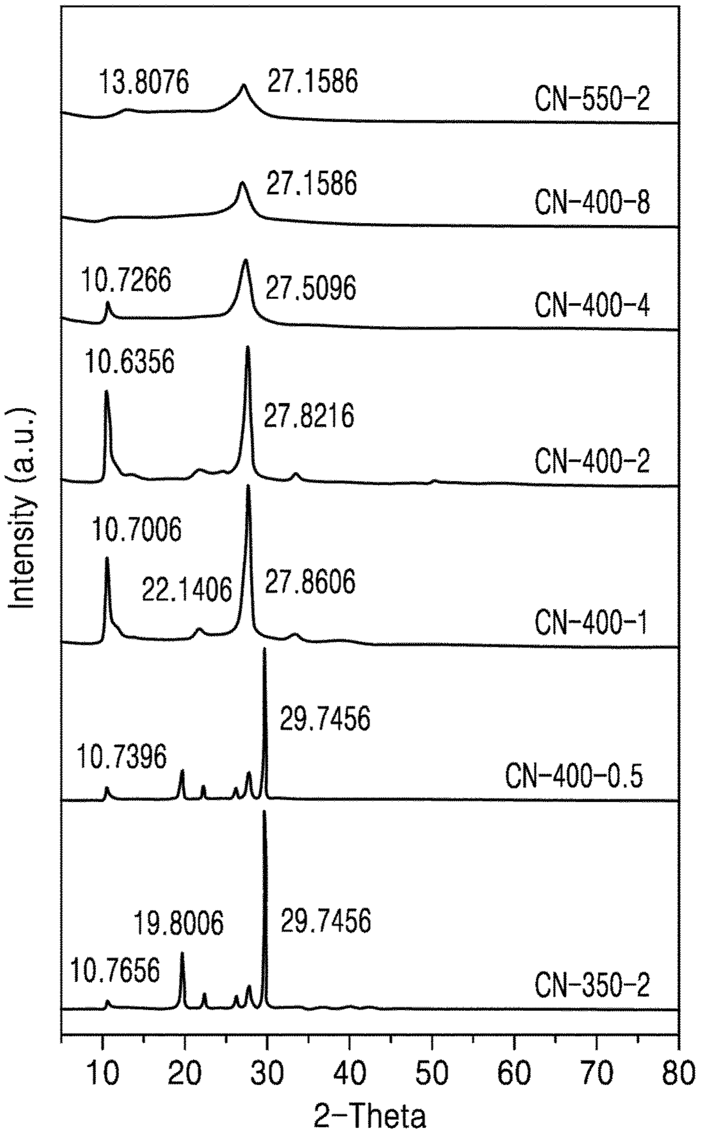
FIG. 3B shows the results confirming the XRD patterns of CN-350-2, CN-400-0.5, CN-400-1, CN-400-2, and CN-400-8 and the XRD patterns of CN-400-4 and CN-550-2.

As confirmed in FIG. 3B, it was confirmed that CN-350-2 a PCN polycondensed at 350° C. for 2 hours, showed diffraction peaks at 10.7656°, 19.8006°, and 29.7456°, it was confirmed that CN-400-0.5 a PCN polycondensed at 400° C. for 0.5 hours, showed diffraction peaks at 10.7396° and 29.7456°, it was confirmed that CN-400-1 a PCN polycondensed at 400° C. for 1 hour, showed diffraction peaks at 10.7006°, 22.1406°, and 27.8606°, it was confirmed that CN-400-2 a PCN polycondensed at 400° C. for 2 hours, showed diffraction peaks at 10.6356° and 27.8216°, it was confirmed that CN-400-4 a PCN polycondensed at 400° C. for 4 hours, showed diffraction peaks at 10.7266° and 27.5096°, it was confirmed that CN-400-8 a PCN polycondensed at 400° C. for 8 hours, showed a diffraction peak at 27.1586°, and it was confirmed that CN-550-2 a PCN polycondensed at 550° C. for 2 hours, showed diffraction peaks at 13.8076° and 27.1586°.

Figure 3C:
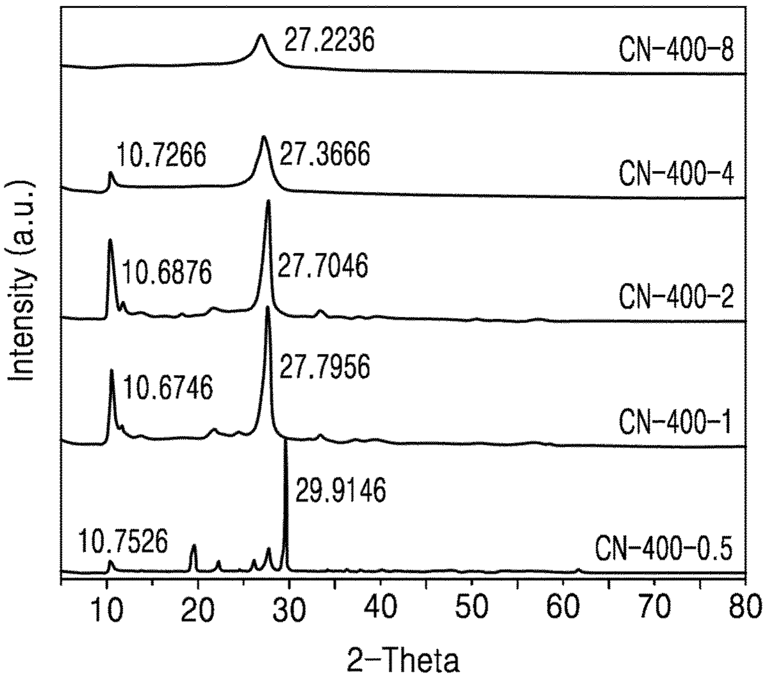
FIG. 3C shows the results confirming the XRD of PCNs (CN-400-0.5, CN-400-1, CN-400-2, CN-400-4, and CN-400-8) produced at a polycondensation temperature of 400° C.

In addition, as confirmed in FIG. 3C, it was confirmed that CN-400-0.5 a PCN polycondensed at 400° C. for 0.5 hours, has diffraction peaks at 10.7526° and 29.9146°, it was confirmed that CN-400-1 a PCN polycondensed at 400° C. for 1 hour, has diffraction peaks at 10.6746° and 27.7956°, it was confirmed that CN-400-2 a PCN polycondensed at 400° C. for 2 hours, has diffraction peaks at 10.6876° and 27.7046°, it was confirmed that CN-400-4 a PCN polycondensed at 400° C. for 4 hours, showed diffraction peaks at and 27.3666°, and it was confirmed that CN-400-8 a PCN polycondensed at 400° C. for 8 hours, showed a diffraction peak at 27.2236°.

3.3 Confirmation of Properties of PCN by FT-IR Spectroscopy

To specifically confirm the crystal structure analysis of the produced PCNs, the chemical structure of the produced PCN samples were confirmed by FT-IR spectroscopy. The results of confirming the IR of CN-400-4 and CN-550-2 by the FT-IR spectrum are shown in FIG. 4A, and the results of simultaneously confirming the IR values of CN-350-2, CN-400-0.5, CN-400-1, CN-400-2, CN-400-8, CN-400-4, and CN-550-2 are shown in FIG. 4B.

Figure 4A:
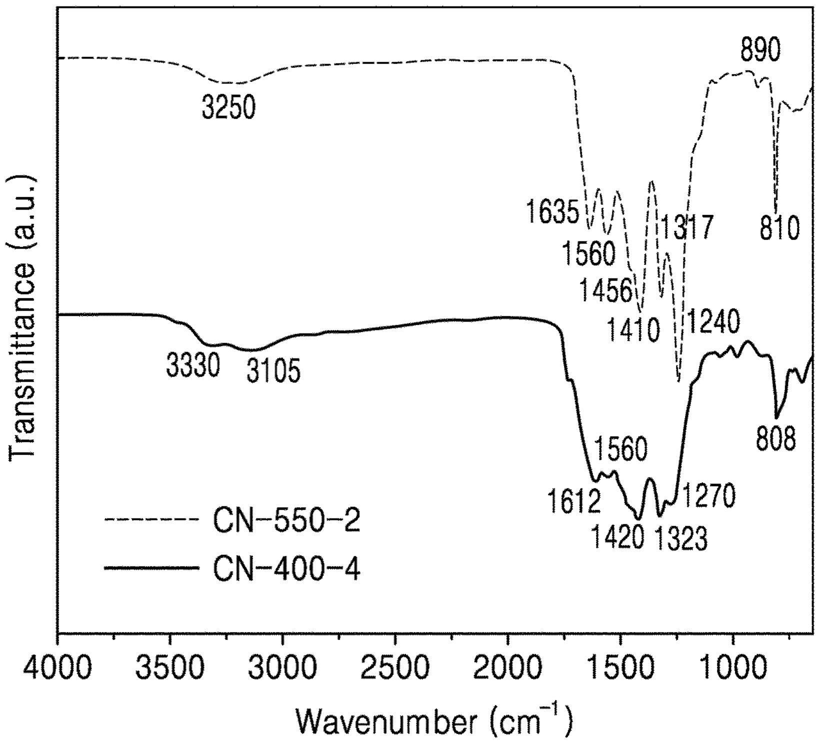
FIG. 4A shows the results confirming the IR of CN-400-4 and CN-550-2 as a result of confirming the chemical structure of a produced PCN sample by FT-IR spectroscopy.

As confirmed in FIG. 4A, it was confirmed that CN-550-2 showed peaks at 810, 890, 1240, 1317, 1410, 1456, 1560, 1635, and 3250 $cm^{-1}$. It was confirmed that CN-400-4 showed peaks at 808, 1270, 1323, 1420, 1560, 1612, 3105, and 3330 $cm^{-1}$. It was confirmed that the FTIR spectrum of CN-550-2 was similar to that of bulk g-C3N4, but the absorption band of the CN-400-4 sample (thermal condensation at 400° C. for 4 hours) showed a broad peak. It was confirmed that the result of confirming such IR peaks by FT-IR analysis was due to the formation of an intermediate product and incomplete polymerization similar to the XRD study.

Figure 4B:
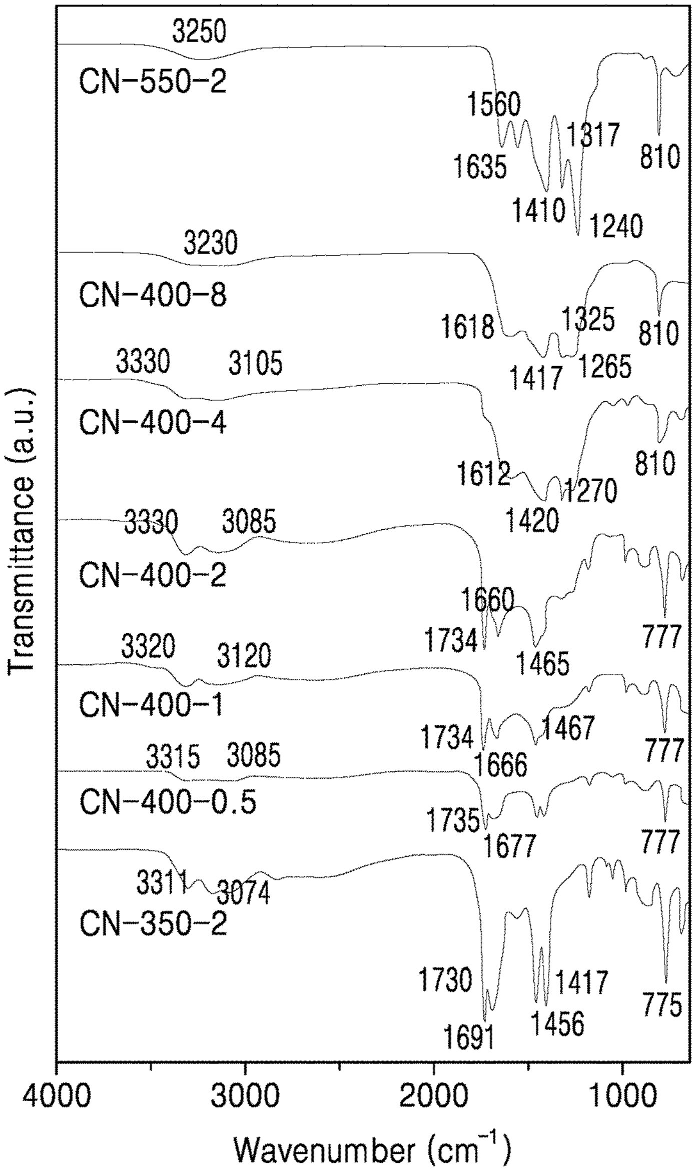
FIG. 4B shows the results confirming the IR of CN-350-2, CN-400-0.5, CN-400-1, CN-400-2, CN-400-8, CN-400-4, and CN-550-2 as a result of confirming the chemical structure of a produced PCN sample by FT-IR spectroscopy.

As confirmed in FIG. 4B, it was confirmed that CN-350-2 showed peaks at 775, 1417, 1456, 1691, 1730, 3074, and 3311 $cm^{-1}$. It was confirmed that CN-400-0.5 confirmation peaks at 777, 1677, 1735, 3085, and 3315 $cm^{-1}$. It was confirmed that CN-400-1 confirmation peaks at 777, 1467, 1666, 1734, 3120, and 3320 $cm^{-1}$. It was confirmed that CN-400-2 showed peaks at 777, 1465, 1660, 1734, 3085, 3330 $cm^{-1}$. It was confirmed that CN-400-4 showed peaks at 810, 1270, 1420, 1612, 3105, and 3330 $cm^{-1}$. It was confirmed that CN-400-8 showed peaks at 810, 1265, 1325, 1417, 1618, and 3230 $cm^{-1}$. It was confirmed that CN-550-2 showed peaks at 810, 1240, 1317, 1410, 1560, 1635, 3250 $cm^{-1}$.

Example 4. Confirmation of Surface Morphology and Microstructure of PCN

Scanning electron microscope (SEM) images were obtained by field emission (FE)-SEM (JEOL JSM-7401F, JEOL). Powder samples were coated with a thin Pt layer by sputter (Hitachi Sputter, E-1045) and examined by SEM.

The surface of the heterogeneous UV filter ingredient particles plays an important role in producing UV-blocking agents that are free of opacity, which is a common concern with metal oxides containing UV-blocking agents. To confirm the surface morphology and microstructure, CN-400-4, CN-400-2 and CN-550-2, were analyzed by FE-SEM and transmission electron microscope (TEM), the results were confirmed by atomic force microscope (AFM), and the results of measuring the thickness of the PCN 2D thin nanosheets produced are shown in FIGS. 5, 6 and 7, respectively.

Figure 5:
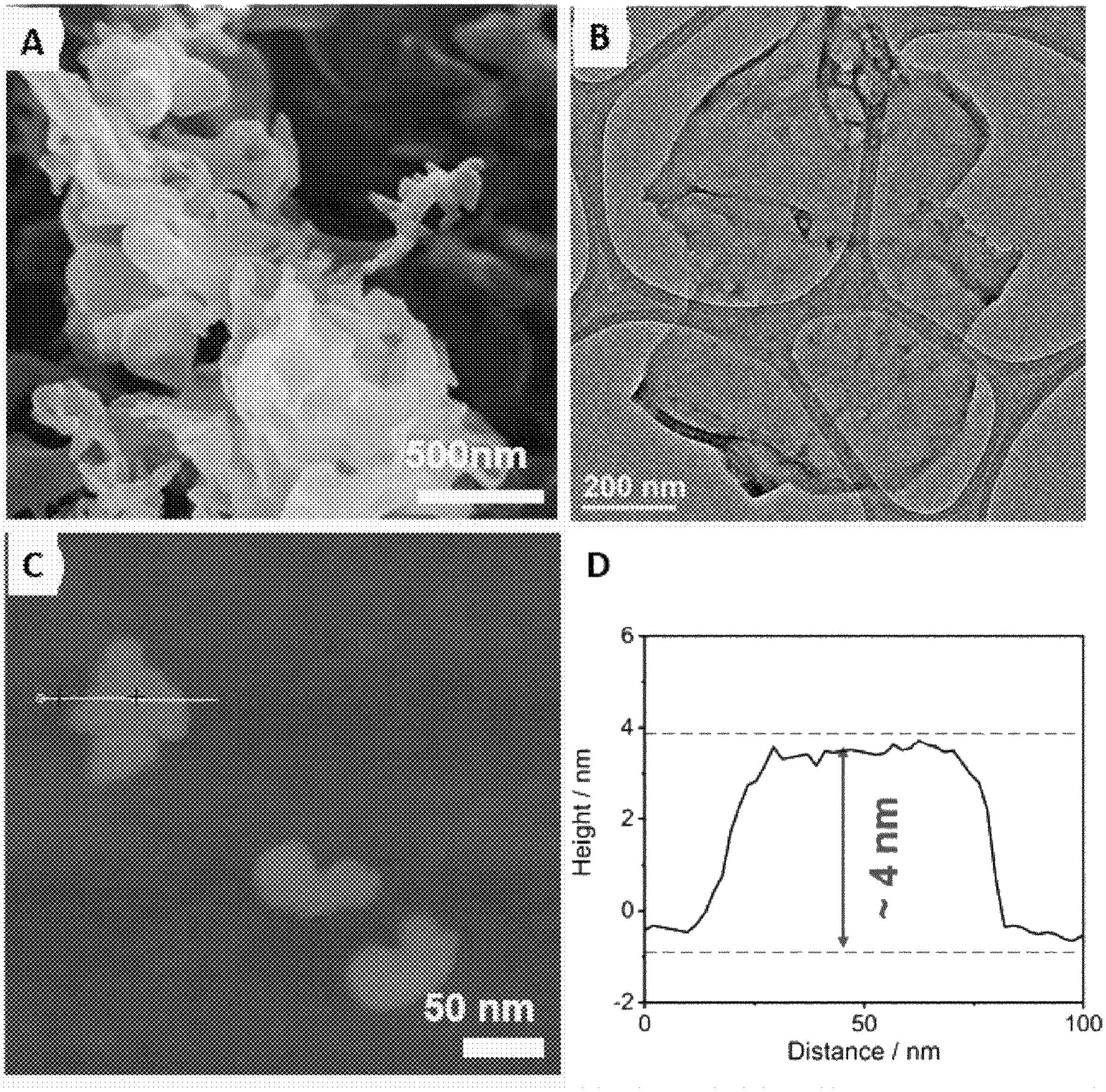
FIG. 5 shows the result of checking the surface of CN-400-4 with a scanning electron microscope (SEM) (A), the result of checking with a transmission electron microscope (TEM) (B), the result of checking with an atomic force microscope (AFM) (C), and the result of confirming the height of particles thereof (D).
Figure 6:
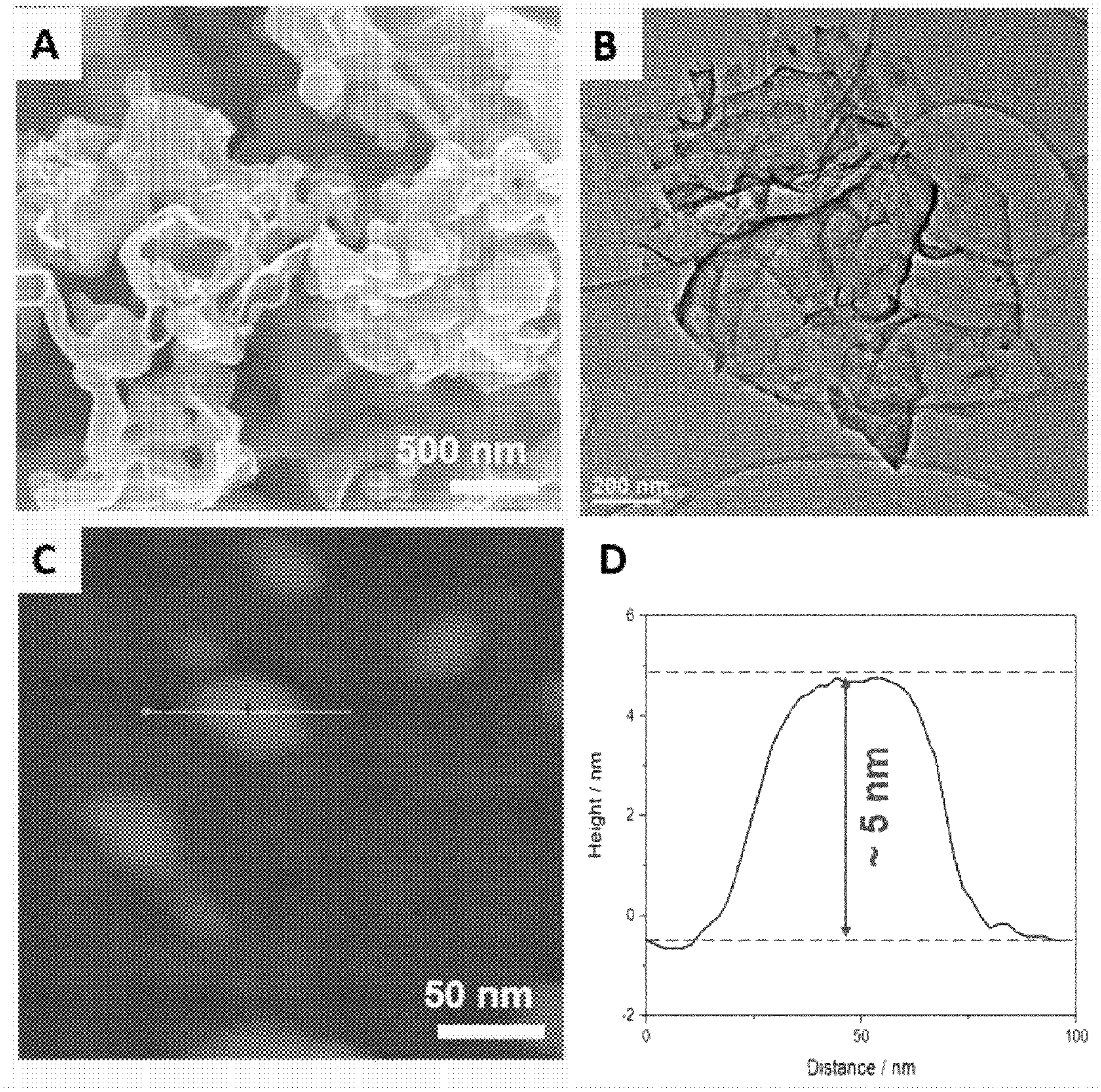
FIG. 6 shows the result of checking the surface of CN-400-2 with an SEM (A), the result of checking with a TEM (B), the result of checking with an AFM (C), and the result of confirming the height of particles thereof (D).
Figure 7:
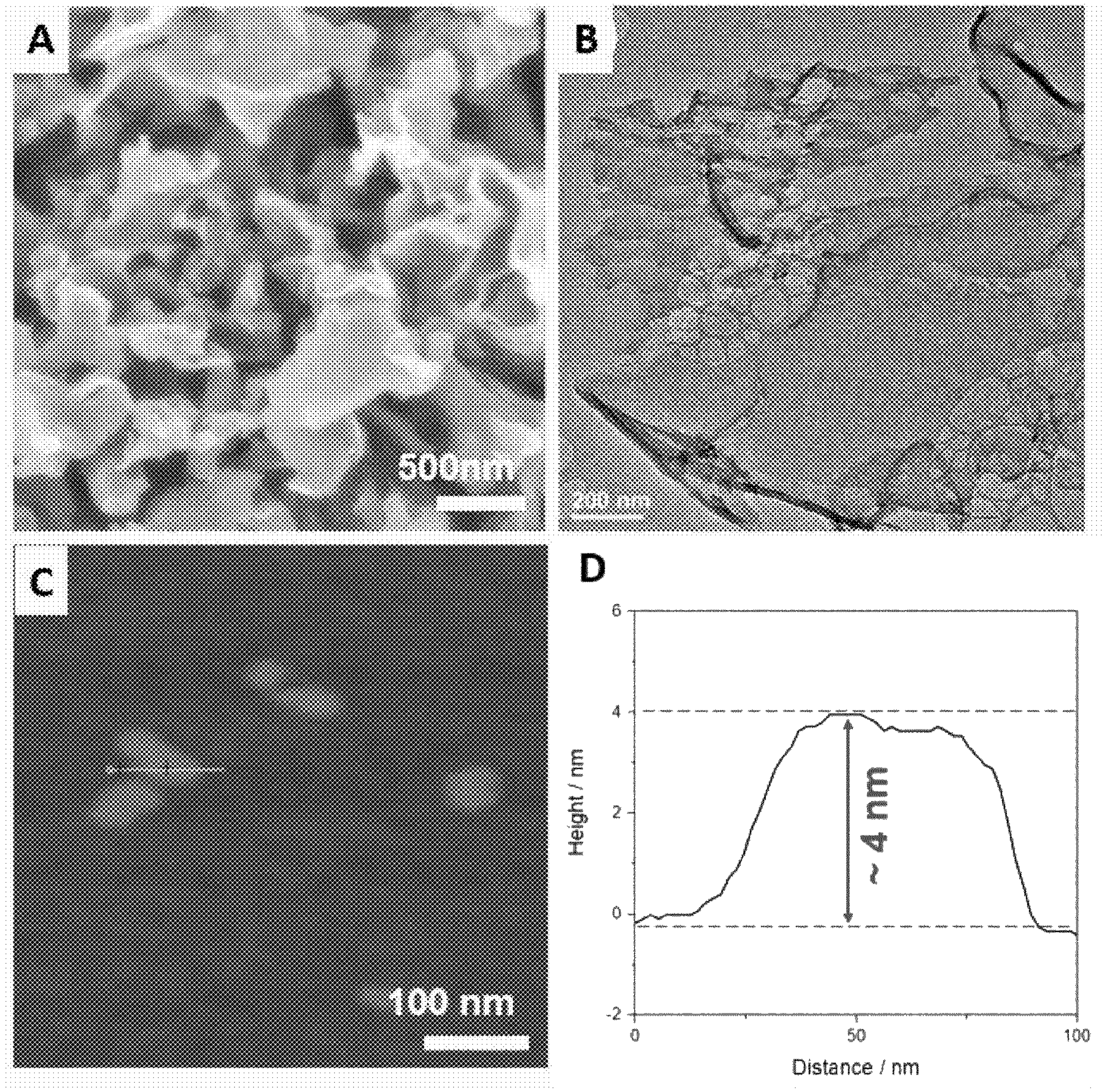
FIG. 7 shows the result of checking the surface of CN-550-2 with an SEM (A), the result of checking with a TEM (B), the result of checking with an AFM (C), and the result of confirming the height of particles thereof (D).

As confirmed in A of FIG. 5, A of FIG. 6, and A of FIG. 7, FE-SEM micrographs showed hierarchical polymer scaffolds with relatively rough surface morphology, confirming the contribution to the sheet structure of both samples, thereby confirmed the rough surface morphology of the produced PCN related to the polymerization conditions. As confirmed in B of FIG. 5, B of FIG. 6, and B of FIG. 7, the TEM images confirmed that all three produced PCN samples were crumpled two-dimensional nanosheet with some ripples and wrinkles on the surface, and the TEM images also confirmed that the produced PCN sheet had high transparency with a smooth texture, with sheet sizes varying from a few nanometers to micrometers.

As confirmed in C and D of FIG. 5, C and D of FIG. 6, and C and D of FIG. 7, the analysis of AFM images and their corresponding height profiles showed that the thickness of the PCN 2D nano sheet was less than 4 nm in the CN-400-4 sample and the CN-550-2 sample and less than 5 nm in the CN-400-2 sample. This confirmed the formation of a useful nano sheet thickness that effectively covers the skin surface in all three samples.

Example 5. Confirmation of ROS Generation Inhibitory Effect of PCN by Quantitative and Qualitative Analysis of Reactive Oxygen Species 5.1 Photochemical Dye Degradation Photocatalytic degradation of RhB was carried out in a pyrex reactor, and a 300 W Xe lamp (Xe Arc lamp source, Oriel) equipped with a 1 solar filter (Oriel) was used as a light source. The light intensity was measured at 100 mW/cm 2 using a silicon detector (Peccell Technologies, Japan). A powder of 10 mg was added to a solution of RhB containing 100 mL of deionized water and 1 mg of RhB, and dispersed by ultrasonics wave for 10 minutes. To confirm the adsorption/desorption equilibrium, the suspension was kept in the dark with continuous stirring for 24 hours. After 24 hours, illumination was applied and photocatalytic degradation of RhB was performed. 5 mL of the suspension was extracted at 10 minute intervals during the 1 hour reaction including the equilibrium point. The extracted suspension was centrifuged for 20 minutes to precipitate the powder. After centrifugation, absorbance of the solution was collected by UV-Vis spectrum using UV-3600, Shimadzu. The photocatalytic activity was compared with the change in the intensity of the absorption peak at 552 nm.

5.2 Method of Fluorescence Probe

The OH radical was measured using a fluorescence probe method. Since coumarin reacts with OH radicals to form umbelliferone with a fluorescence peak at 455 nm, coumarin was used to detect OH radicals generated by $TiO_2$, ZnO, and the produced PCN in the UV-blocking agent. Therefore, using this method, it was possible to compare the fluorescence intensity at 455 nm of all samples to find out which sample generated higher concentrations of OH radicals. 50 mg of $TiO_2$, ZnO, and the produced PCN were added to 20 mL of 0.03 mM coumarin solution. The suspension was irradiated for 120 seconds at an intensity of 100 mW/cm$^2$ in a Xe Lamp with one solar filter. 5 mL of the suspension was extracted before irradiation and 60 seconds and 120 seconds after irradiation. The extracted suspension was centrifuged for 20 minutes. And the fluorescence spectrum of umbelliferone was obtained with a fluorescence intensity meter (Cary Eclipse, Varian). Afterwards, it was confirmed that the fluorescence intensity at 455 nm was proportional to umbelliferone by calibration.

5.3 Confirmation of ROS Generation Inhibitory Effect of PCN by Comparison with $TiO_2$ and ZnO Used in Commercialized UV Filter Ingredients It is known that encapsulation or coating of UV filter ingredients in a matrix of some inorganic, polymeric, and bioadhesive materials can effectively remove, if not prevent, the generation of ROS. However, 100% encapsulation of UV filter ingredients is not an easy process, and in the absence of cover of UV filter ingredients, the surface can still generate ROS, therefore a highly efficient flat-band position engineering PCN UV filter ingredient was produced to prevent generation of ROS. The concentration of ROS generated by the produced PCN is low, which is due to the reduction and oxidation of $O_2$ and $H_2O$ to $O_2$*− and *OH, respectively, due to the unfavorable flat-band positions (conduction band (CB) and valence band (VB)), therefore the confinement of the generated ROS is not required. Since the concentration of photogenerated ROS for UV filter ingredients plays a crucial role in the application of UV filter ingredients in commercial UV-blocking agents, various ROS analytical methods were applied for the qualitative and quantitative evaluation of $O_2$*− and *OH, which exhibit a high degree of sensitivity and accuracy. In order to accurately measure ROS generation, quantification analysis was performed by chemical analysis, direct dye degradation, photoluminescence spectroscopy by detection of fluorescent products, and UV-visible absorption spectroscopy.

Figure 8A:
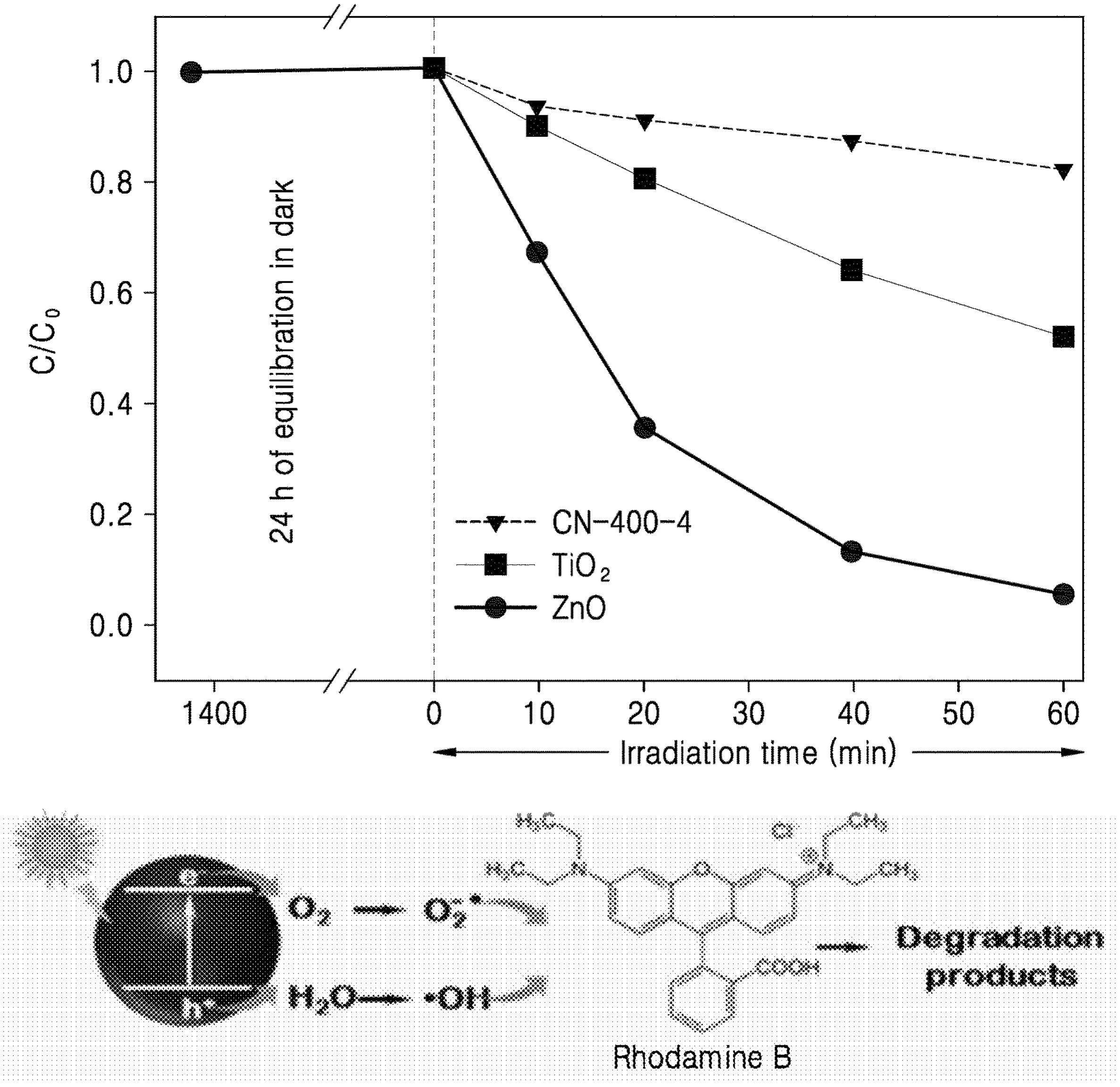
FIG. 8A shows the results of confirming the degree of ROS generation of TiO2, ZnO, and CN-400-4 by photocatalyst decomposition analysis of RhB.

The ROS generation tendency of the produced PCN was analyzed by examining the dye gradient potential value and an experiment was conducted to compare with commercialized $TiO_2$ and ZnO particles, result is shown in FIG. 8A. Primary ROS are highly reactive and rapidly react with organic molecules or dyes present in the reaction solution, and the photocatalytic dye degradation tendency of such commercialized UV filter ingredients compared to the produced PCN was confirmed by the photodegradation of rhodamine B (RhB) in aqueous solution under UV visible light irradiation, and ROS generation was evaluated. The reaction of ROS and RhB to the produced PCN and the commercialized UV filter ingredient is shown are FIG. 8A.

As confirmed in FIG. 8A, the slow RhB dye degradation rate in the produced PCN suspension confirmed that the amount of ROS generation from the produced PCN nanosheets under light irradiation was quite small. However, when a commercialized UV filter ingredient was applied, strong photochemical dye degradation activity was confirmed. In particular, as can be confirmed in FIG. 8A, when $TiO_2$ particles were added to the RhB solution, almost 50% of RhB degradation appeared after 60 minutes of irradiation, and when ZnO particles were added, up to about 95% dye degradation appeared, confirming that the ROS generation rate was high in the case of such metal oxides. Such results confirm that $TiO_2$ and ZnO have suitable flat-band positions to generate both ROS ($O_2$*− and *OH), while the produced PCN is inefficient in generating *OH and has little potential to generate $O_2$*−.

Figure 8B:
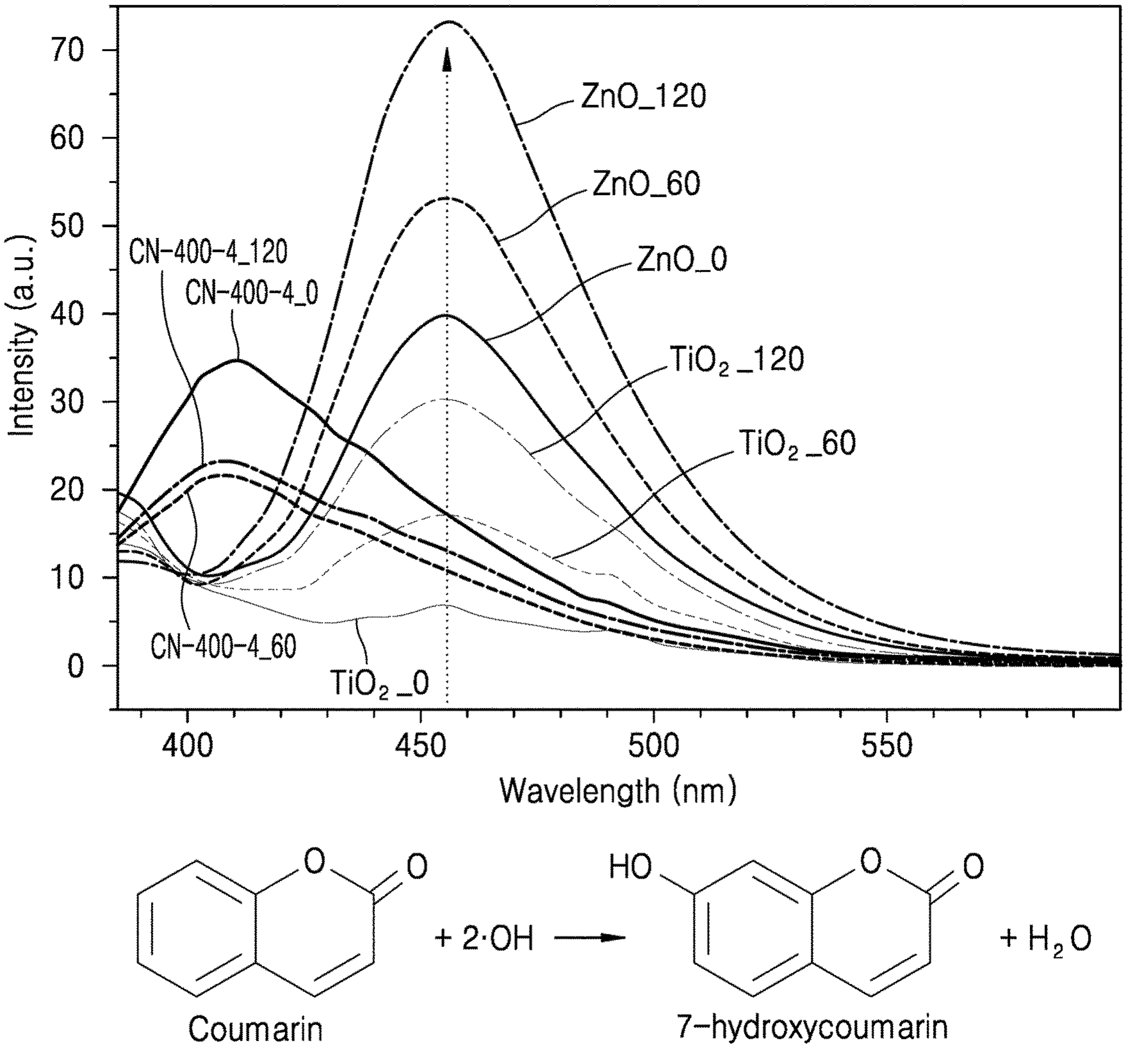
FIG. 8B shows the results of quantitative analysis of ROS generation of TiO2, ZnO, and CN-400-4 by fluorescence probe analysis that detects OH radicals using coumarin.

Photoluminescence spectroscopy and XTT colorimetric experiments were conducted to further quantify the *OH and $O_2$*-radical concentrations for the UV filter ingredients, respectively. After reacting the produced PCN, $TiO_2$ and ZnO suspension solution under UV visible light irradiation for 1 hour and 2 hours, the fluorescence spectrum of the coumarin solution and the fluorescent 7-hydroxycoumarin compound generated from the reaction of coumarin with *OH were confirmed and shown in FIG. 8B. As confirmed in FIG. 8B, it was confirmed that the dotted arrow corresponding to $\lambda_{MAX}$ 455 nm for 7-hydroxycoumarin indicates an increase in the peak intensity with the increase in the concentration of *OH radicals during the photochemical reaction process, which is equivalent to the increase in the concentration of *OH radicals during the photochemical reaction process. As confirmed in FIG. 8A and FIG. 8B, which are the results of the dye degradation experiment, the results of the photoluminescence experiment confirm that ZnO is the most photoactive material. The concentration of *OH radical was quantified using a calibration curve for 7-hydroxycoumarin in deionized water. By such results, it was confirmed that the UV filter ingredient produced of the produced PCN has no or negligible generation of *OH radicals and does not generate *OH radicals, therefore the produced PCN UV filter ingredient can be used without carcinogenic ROS.

As confirmed in the example above, the PCN UV filter ingredient produced by the result of ROS analysis generate much less ROS than commercialized $TiO_2$ and ZnO UV filter ingredients, and the amount of ROS generated is such that it can be seen that there is no ROS generation, therefore, it was confirmed that surface shielding and encapsulation are not required to inhibit ROS generation and can be directly used for products that can block UV.

5.4 Confirmation of Photoluminescence Effect of PCN

The photoluminescence effect of the produced PCN and commercialized UV filter ingredients (ZnO and $TiO_2$) was analyzed.

Specifically, the samples were excited at about 300 nm using a photoluminescence measurement device and the photoluminescence seen in the wavelength range after about 320 nm was measured. Photoluminescence occurs when excited electrons and holes move to the surface and meet and recombine before participating in a chemical reaction, and more photoluminescence means that more excited electron-hole pairs are not used for other chemical reactions.

Figure 8C:
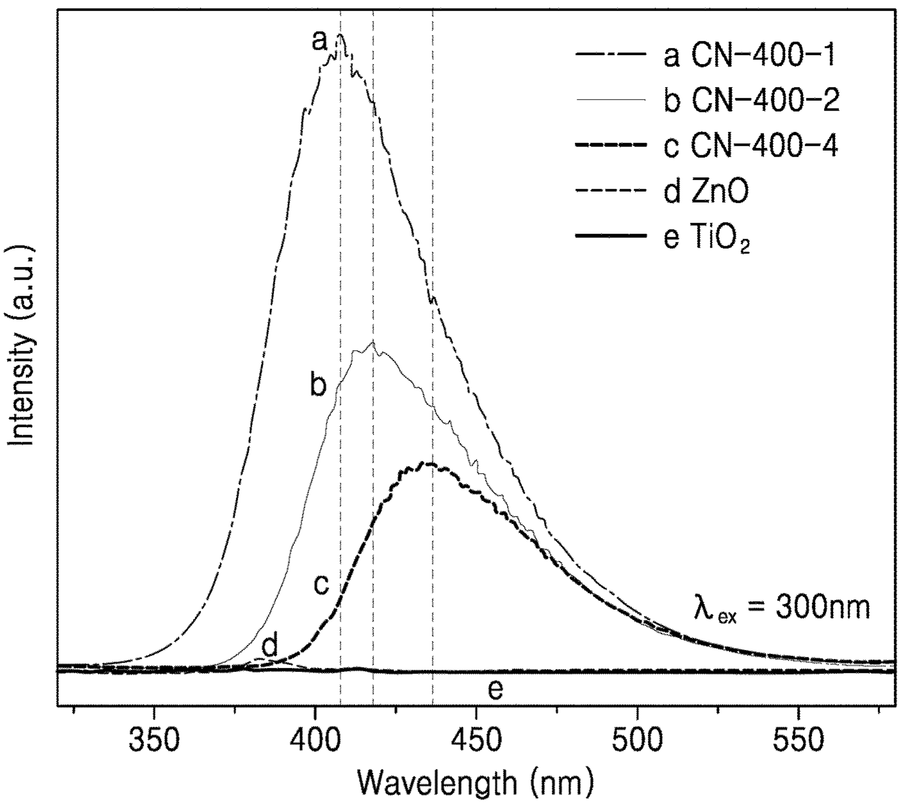
FIG. 8C shows the results of confirming the photoluminescence effect of TiO2, ZnO, CN-400-1, CN-400-2, and CN-400-4.

As shown in FIG. 8C, it was confirmed that $TiO_2$ and ZnO exhibit little photoluminescence, while the produced PCNs (CN-400-1, CN-400-2, and CN-400-4) exhibit a large amount of photoluminescence. In particular, it was confirmed that the photoluminescence effect of CN-400-1 was the best among the produced PCNs.

From this example, it can be inferred that in the case of $TiO_2$ and ZnO, most of the excited electrons reach the surface and are used for chemical reactions such as ROS generation reactions, which supports the high photocatalytic activity of $TiO_2$ and ZnO as confirmed in Example 5.3 above. In addition, it can be inferred from this example that, unlike $TiO_2$ and ZnO, the produced PCN does not use the excited electron-hole pairs for other chemical reactions, which supports the low photocatalytic activity of the produced PCN as confirmed in Example 5.3 above.

Example 6. Confirmation of UV-Blocking Effect of PCN 6.1 Confirmation of PCN UVR Absorption Effect by Comparison with Commercialized $TiO_2$ and ZnO UV Filter Ingredients In order to be able to protect the skin from UV, it is necessary to absorb UV to prevent the harmful effects of sunlight, therefore the degree of UVR absorption by the produced PCN was measured to confirm the effectiveness of the UV-blocking material, and the UV-Vis diffuse reflectance spectrum for the produced PCN, $TiO_2$, and ZnO were confirmed, and the results are shown in FIG. 9A.

Specifically, the UV-Vis diffuse reflectance spectrum of the sample powder samples were obtained using a UV-Vis diffuse reflectance spectrophotometer (UV-3600, Shimadzu) equipped with an integrating sphere (ISR-240A, Shimadzu), and $BaSO_4$ was used as a reference. The band gap energy of the samples was confirmed by Tauc-plot from the kubelka-munk transformation of the diffuse reflectance spectrum.

Figure 9A:
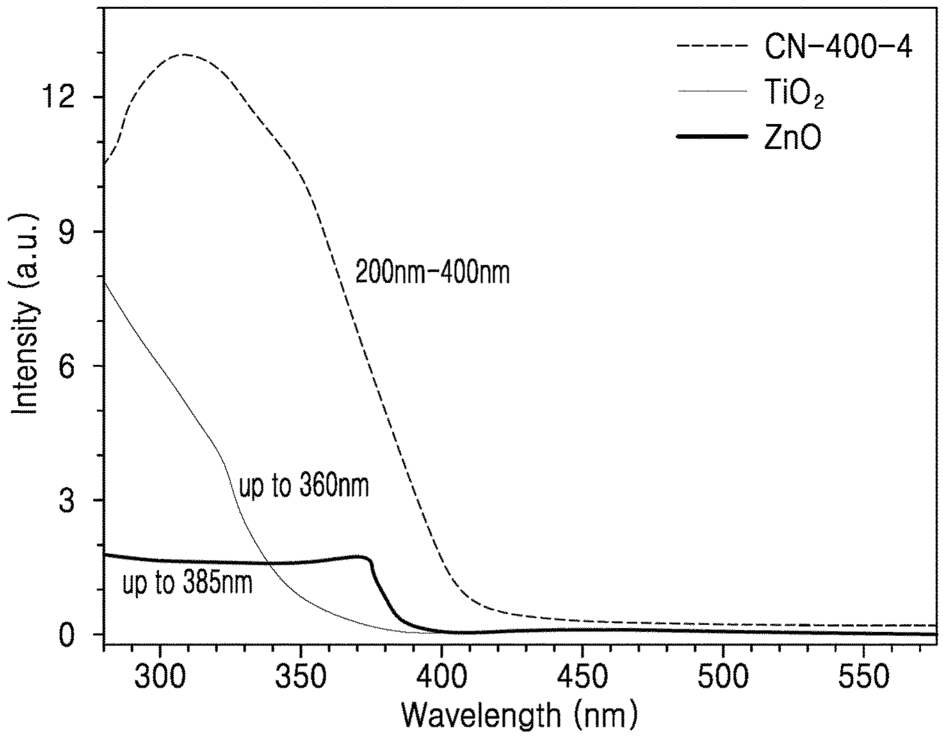
FIG. 9A shows the results of confirming the UV-Vis diffuse reflectance spectrum of TiO2, ZnO, and CN-400-4.

As confirmed in FIG. 9A, it was confirmed that $TiO_2$ particles showed absorption only up to 360 nm, while ZnO covered up to 385 nm. However, it was confirmed that the produced PCN covers the entire UV spectrum (200 nm to 400 nm) and can protect the skin from harmful UVA and UVB radiation.

6.2 Measurement of UV-Blocking Factor (SPF) and Protective Effects from UVA (PA) of PCN The produced PCN (CN-400-4, etc.) samples were mixed with moisturizing cream (SPF=1) or sunscreen (SPF=15) using a magnetic stirrer at 600 rpm for 24 hours. The entire blending process was carried out at room temperature in a dark room. The sunscreen includes an inorganic UV-blocking agent (titanium dioxide) and organic UV-blocking agents (octocrylene, butylmethoxydibenzoylmethane, ethylhexyltriazone, terephthalylidene dicamphorsulfonic acid), which are commercialized UV filter ingredients, and the mixed sample of the sunscreen and produced PCN was produced to contain about 10% of the produced PCN. The moisturizing cream mixed samples were produced to include about 1% and about 5% of the produced PCN, and as a control group, instead of the produced PCN, samples in which commercialized UV filter ingredients such as avobenzone, oxybenzone, ZnO, and $TiO_2$ were mixed with the moisturizing cream were used.

After mixing, the produced PCN mix samples, that is, the mixed sample of produced PCN with moisturizing cream (SPF=1) and the mixed sample of produced PCN with sunscreen (SPF=15), were applied to a 3M Transpore tape (7.5 $cm^2$) attached to a clean quartz plate surface. The samples (2 $mg/cm^2$) were distributed and then spread over the entire surface by slowly rubbing the plate surface with a thimble-coated finger. The prepared samples were dried in the dark and shielded from light for 20 minutes.

UV transmittance was measured using a Cary 50 UV-vis spectrophotometer equipped with a solid sample holder (Agilent Technologies, USA). Four spots were scanned for each sample and each data was measured in the range from UVB (290 nm to 320 nm) to UVA (320 nm to 400 nm). All transmittance data was collected at 1 nm intervals. After measuring the UV transmittance, an in vitro evaluation of the UV-blocking factor (SPF) was conducted using the following equation.

$$SPF = \sum_{290}^{400} E_\lambda S_\lambda / \sum_{290}^{400} E_\lambda S_\lambda T_\lambda$$

Where Eλ is the erythema spectral effect, Sλ is the solar spectral effect, and Tλ is the spectral transmittance of the sample.

In addition, the evaluation of UVA protection factor (UVA PF) was conducted using the following equation.

$$UVA\ PF = \sum_{320}^{400} E_\lambda I_\lambda \Delta\lambda / \sum_{320}^{400} E_\lambda I_\lambda T_\lambda \Delta\lambda$$

Where Iλ is the biological action spectrum for UVA. In this case, Eλ and Iλ are equal to 1 for all UVA wavelengths.

As shown in Table 1, it was confirmed that the moisturizing cream mixed samples including each of the produced CN-400-1, CN-400-2, CN-400-4, CN-400-8, and CN-550-2, overall, exhibited higher values of SPF and UVA PF compared to the mixed samples including commercialized UV filter ingredients. In particular, it was confirmed that in the case of the produced CN-400-4 mixed sample exhibited the highest SPF and UVA PF values among the produced PCN mixed samples and significantly higher SPF and UVA PF values compared to the formulated mixed samples containing commercialized UV filter ingredients.

TABLE 1

| | SPF (UVB) | | UVA PF (UVA) | |
|---|---|---|---|---|
| Cream + Sample (wt %) | 1 wt % | 5 wt % | 1 wt % | 5 wt % |
| CN-400-1 | 2.2 | 3.17 | 1.81 | 2.49 |
| CN-400-2 | 2.39 | 6.38 | 1.99 | 4.78 |
| CN-400-4 | 3.36 | 10.79 | 2.66 | 8.1 |
| CN-400-8 | 1.79 | 6.74 | 1.6 | 5.54 |
| CN-550-2 | 1.77 | 4.82 | 1.64 | 4.48 |
| Titanium dioxide | 1.72 | 7.66 | 1.38 | 3.96 |

TABLE 1-continued

| | SPF (UVB) | | UVA PF (UVA) | |
|---|---|---|---|---|
| Cream + Sample (wt %) | 1 wt % | 5 wt % | 1 wt % | 5 wt % |
| Zinc oxide | 1.18 | 2.24 | 1.14 | 2.23 |
| Avobenzone | 1.37 | — | 1.64 | — |
| Oxybenzone | 1.49 | — | 1.19 | — |

Figure 9B:
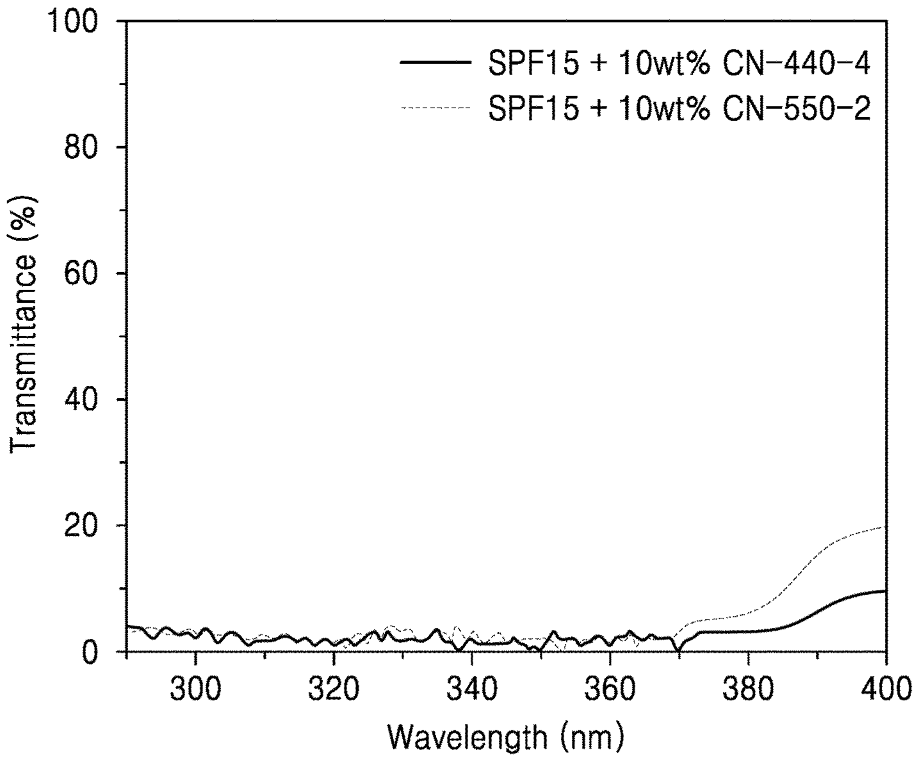
FIG. 9B shows the results of confirming the UV-blocking effect of samples produced by mixing each of CN-400-4 and CN-550-2 with a sunscreen (SPF=15) including a commercialized UV filter ingredient.

In addition, as shown in FIG. 9B, it is confirmed that the sample mixed with the produced CN-400-4 and the sunscreen exhibits a better UV-blocking effect in the UVA region compared to the mixed sample of the produced CN-550-2. Furthermore, by calculating the SPF and UVA PF values, it was confirmed that when the sunscreen with an SPF value of 15 is mixed with 10% of the produced CN-400-4, the final SPF value is 45.4 and the final UVA PF value is 31, and it was confirmed that when the sunscreen with an SPF value of 15 is mixed with 10% of the produced CN-550-2, the final SPF value is 38 and the final UVA PF value is 17.5.

Thus, it was confirmed that the produced PCN exhibits a better UV-blocking effect compared to commercialized UV filter ingredients, and it was confirmed that the produced PCN can be effectively used to produce UV-blocking products with high SPF and UVA PF values, and that by mixing the produced PCN with commercialized UV filter ingredients, the SPF and UVA PF values can be efficiently increased to further maximize the UV-blocking effect.

Example 7. Confirmation of Biological Applications of PCNs as UV-Blocking Agents 7.1 Confirmation of Analysis Conditions of UV Radiation Source and MTT for Bio-Applications The UV radiation source was a 300 W lamp solar stimulator (91160, Newport) and one solar light was irradiated. MTT analysis were obtained on a multimode microplate reader (SpectraMax M5e, Molecular Devices).

7.2 Confirmation of Cytotoxicity of PCN

Cell Culture

NIH-3T3 cells were purchased from American-Type Culture Collection (ATCC, USA). Cells were cultured in a DMEM medium supplemented with 10% fetal bovine serum (FBS), 100 U/mL penicillin, and 100 μg/mL streptomycin. All cells were cultured at 37° C. in a humidified environment of 5% $CO_2$. For MTT analysis, cells were seeded in 96-well plates at a density of $5*10^3$ cells per well. After 24 hours of seeding, a series of concentrations (five concentrations and control groups) of the sample solution were added to each well. After 1 hour of culturing, light was irradiated for 1 minute and then cultured for another 5 hours. 10 μL MTT solution (5 mg/mL) was added to each well, cultured at 37° C. for 2 days, cultured for an additional 4 hours, and then 100 μL of SDS-HCl solution was added to stop the reduction reaction and purple formazan was dissolved. The absorbance of each well at 595 nm was measured with a multimode microplate reader. Cytotoxicity analysis was performed three times, and the average value of the three measurements was obtained.

CLSM Images of NIH-3T3 Cells (ROS Generation)

Confocal laser scanning microscopy (CLSM) images were obtained with an LSM 780 from ZIESS. NIH-3T3 cells at a density of $1*10^4$ were seeded into 8-well Lab-tek II chamber cover glasses (Nunc) for a ROS generation experiment. After growing NIH-3T3 cells in a cell incubator for 24 hours, 20 μg/ml of nanoparticles were added to the cells along with the medium. After culturing for 1 hour, light was irradiated to the cells for 1 minute. After further culturing for 5 hours using the medium, Hela cells were washed 3 times. Mitochondria were stained using mitotracker deep red at a concentration of 1 μM for 10 minutes. After washing the cells with the finished medium, the cells were immediately stored in a CLSM medium.

Live/Dead Analysis

Live/dead analysis images were obtained with an evos fluorescence microscope. NIH-3T3 cells at a density of $5*10^4$ were seeded in 24-well cell culture plates for live/dead analysis. After growing NIH-3T3 cells in a cell incubator for 24 hours, 20 μg/ml of nanoparticles were added to the cells along with the medium. After culturing for 1 hour, light was irradiated to the cells for 1 minute. After another 5 hours of culturing, the Hela cells were washed three times with a medium. Live/dead analysis was used to stain mitochondria at a concentration of 1 μM for 10 minutes. Cells were washed with the finished medium. The medium was replaced with the live/dead imaging solution mixture according to the protocol of the manufacturer. Cell culture was cultured for 20 minutes and imaged by fluorescence microscopy using the green (live cells) and red (dead cells) channels.

Actual Cytotoxicity Confirmation Result of PCN

An experiment was conducted to confirm if the produced PCN with UV-blocking use could have biological applications. An experiment was conducted to confirm if cytotoxicity occurs when CN-400-4 is used among the produced PCNs. To evaluate the biological toxicity, the cell viability assay was evaluated by 3-(4,5-dimethylthiazol-2-yl)-2,5-diphenyltetrazolium bromide (MTT) analysis with NIH-3T3 cells, an embryonic fibroblast cell line, and the results are shown in FIG. 10A, and for the positive control group, ZnO was used under the same experimental conditions, and the experimental result is shown in FIG. 10B.

Figure 10A:
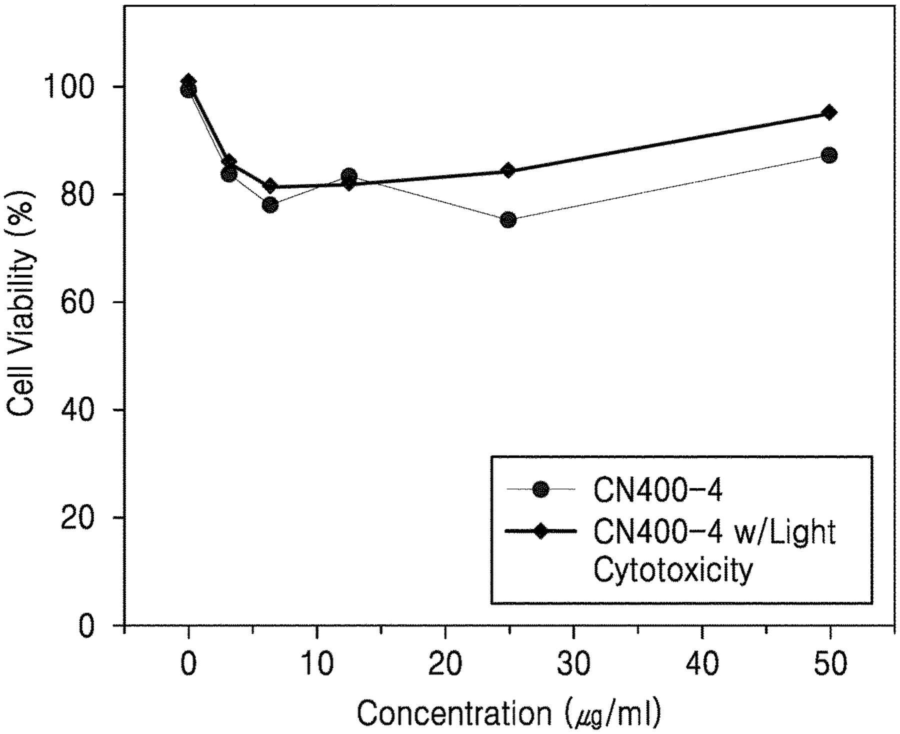
FIG. 10A shows the result of confirming the cytotoxicity of CN-400-4 to embryonic fibroblast cells (NIH-3T3).
Figure 10B:
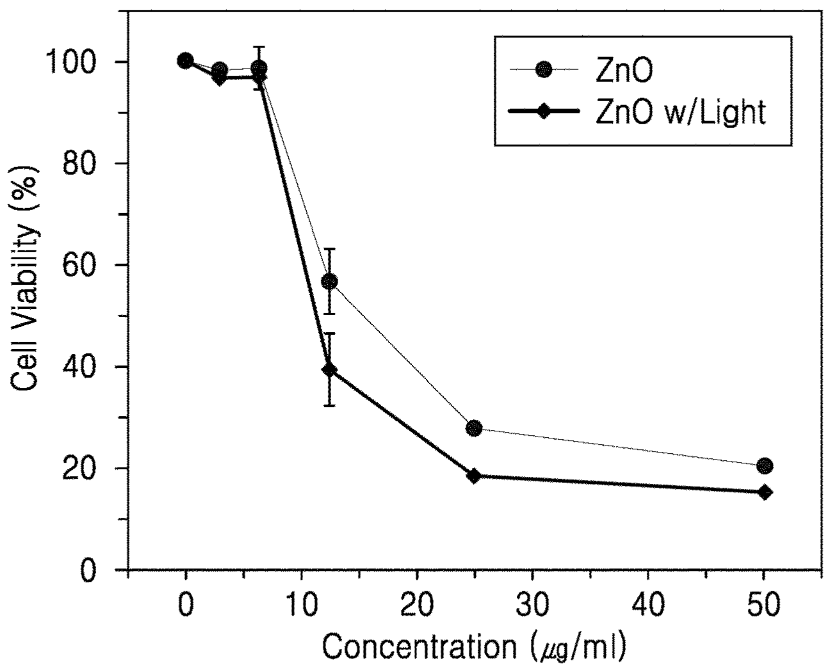
FIG. 10B shows the result of confirming the cytotoxicity of ZnO to embryonic fibroblast cells (NIH-3T3).

As confirmed in FIG. 10A, CN-400-4 was confirmed to be non-toxic to NIH-3T3 cells and did not show any toxicity to the cells even when subjected to UV irradiation for 24 hours for culturing at a maximum concentration of 50 μg/ml. In contrast, as confirmed in FIG. 10B, it was confirmed that compared to CN-400-4, the positive control group ZnO nanoparticle showed 50% viability of NIH-3T3 cells at 10 μg/ml, and when irradiated with UV, the viability decreased to less than 40%.

Figure 10C:
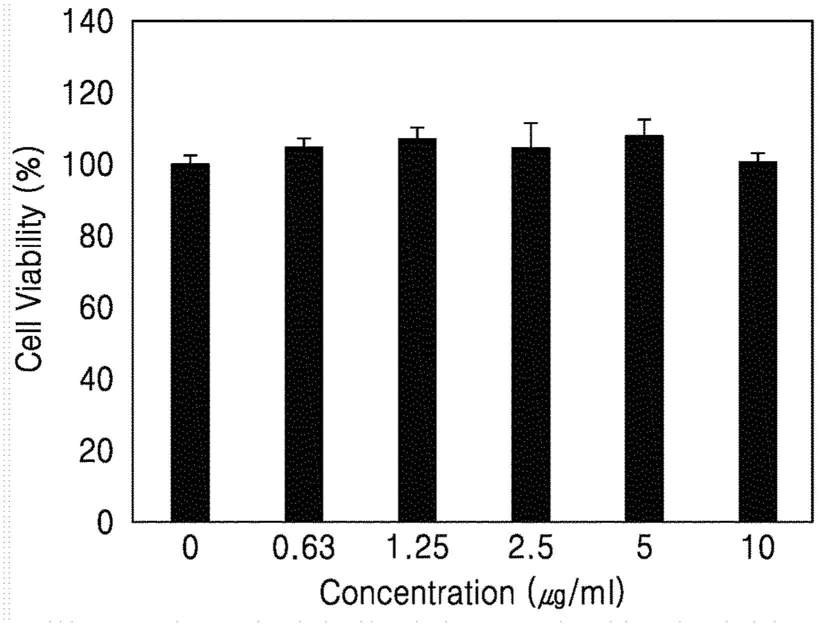
FIG. 10C shows the result of confirming the cytotoxicity of CN-400-4 to human skin fibroblasts (HS-68).

In addition, in order to further investigate the toxicity of the produced CN-400-4 to human skin cells, a human skin fibroblast, HS-68 cell line, was selected, and an experiment was conducted to confirm cytotoxicity and confirm cell viability, the result is shown in FIG. 10C.

As confirmed in FIG. 10C, CN-400-4 was confirmed to be not toxic to HS-68 cells, a human skin cell line, even at concentrations up to 10 μg/ml, resulting in a viability rate of about 90% or more.

Figure 11:
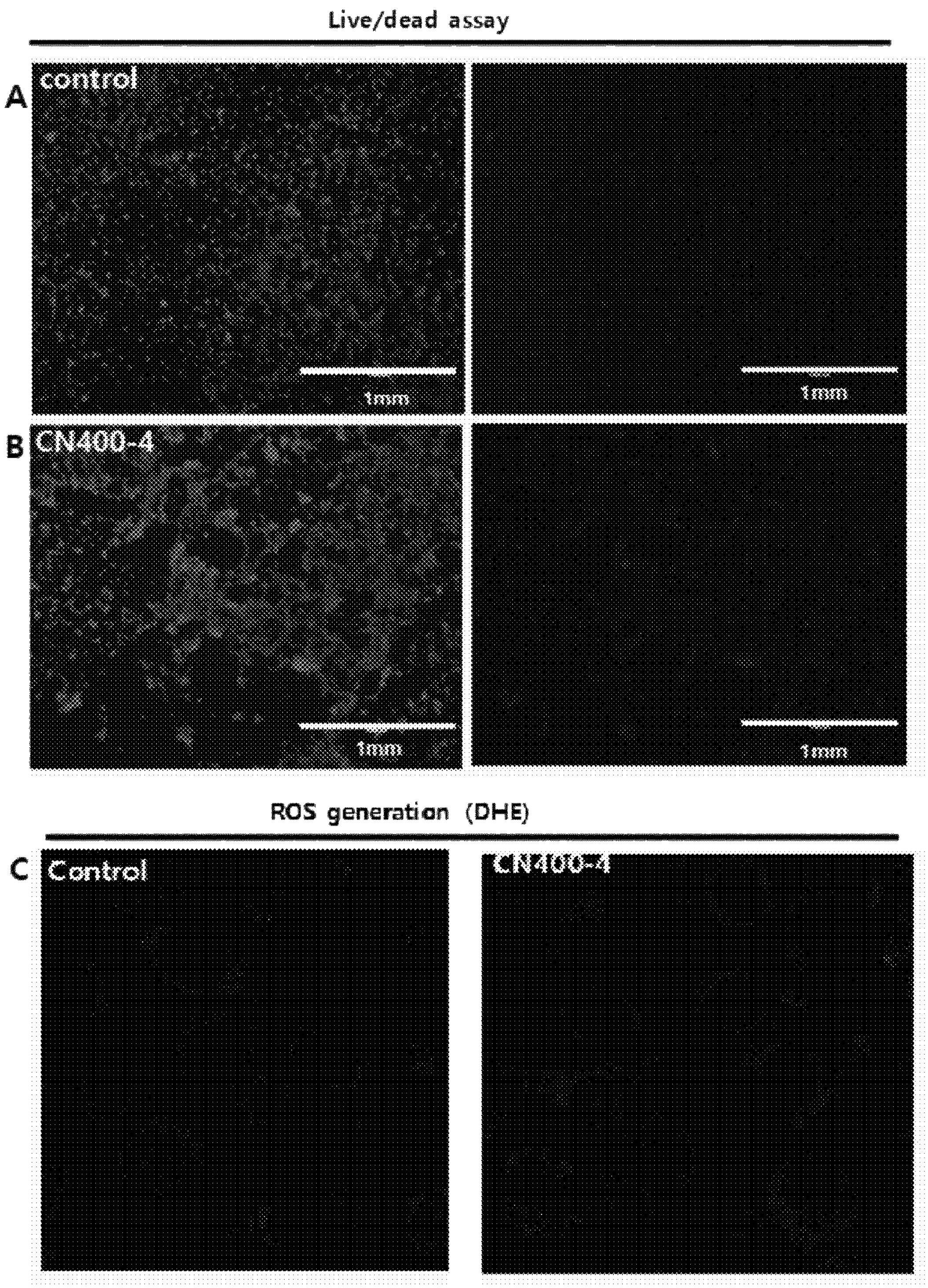
FIG. 11 shows the results (A and B) of evaluating the cell viability by live/dead cell imaging when CN-400-4 was used, and the result of confirming by a ROS indicator dihydroxyethidium (DHE) for visualization (C).

In addition, the cell viability when CN-400-4 was used was also evaluated by life/dead cell imaging, and are shown in A and B of FIG. 11. As confirmed in A and B of FIG. 11, it was confirmed that when irradiated with light including UV, after 6 hours of culture CN-400-4 was not toxic to a similar extent when compared to untreated NIH-3T3 cells, showing bright green fluorescence indicating viable cells, and almost no red fluorescence indicative of dead cells. Furthermore, in order to prove that CN-400-4 rarely generate reactive oxygen species (ROS) in cells, dihydroxyethidium (DHE), an indicator of ROS inside cells, was used for visualization and is shown in C of FIG. 11. As confirmed in C of FIG. 11, it was confirmed that CN-400-4 generate no ROS in NIH-3T3 under light irradiation, similar to the untreated control group NIH-3T3 under light irradiation.

7.3 Confirmation of Skin Protection of PCN as a UV-Blocking Agent

UV Exposure to Micropig® Franz Cell Membrane (FCM) (Histological Analysis)

Micropig® Franz Cell Membrane (FCM) with a size of 2 cm×2 cm×600 μm was purchased and used from APURES Co. Ltd. Nanoparticles were added to 12 wells containing FCM. After 1 hour of culturing, light was irradiated with a solar simulator for 30 minutes. After another 3 hours of culturing, the wells were washed three times with PBS. The FCM was stored in NBF solution overnight. For histochemical staining, the fixed FCM was dehydrated by a concentration gradient ethanol wash, embedded in paraffin blocks, sectioned, stained with H&E stain, and analyzed.

Confirmation of Ex Vivo Skin Penetration Probe of PCN by SEM Images of FCM

CN-400-4 nanoparticles were added to 12 wells containing FCM, and PBS solution was added to the FCM. After 4 hours of culturing, the FMC was washed three times with PBS. The washed FCM was lyophilized and subjected to SEM. Samples were prepared by Pt sputter coating at 20 mA electric current for 60 seconds using a hitachi sputter.

Confirmation of Skin Protection Effect of PCN

Figure 12:
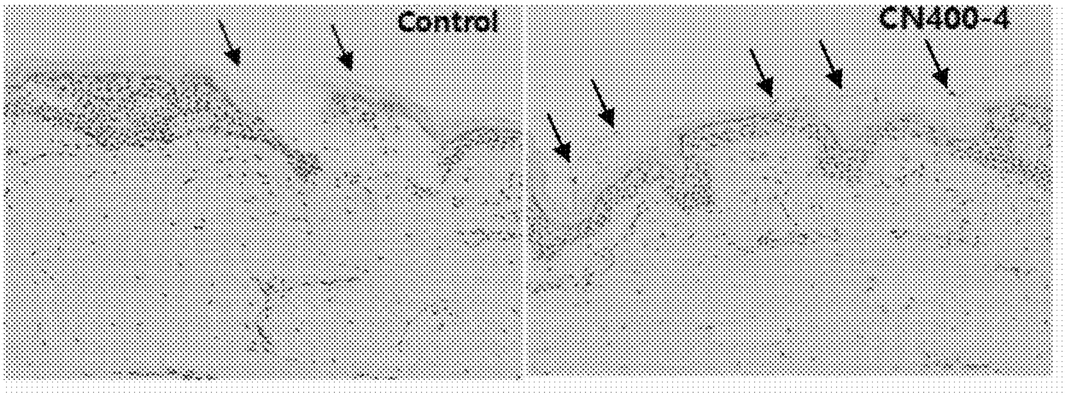
FIG. 12 shows the result of confirming by performing H&E staining to confirm the degree of skin damage by comparing, with an untreated control group, a case where CN-400-4 was treated in FCM and cultured for 4 hours.

To be effective as a UV-blocking agent, PCN must remain in the stratum corneum, the surface of the skin, without penetrating the epidermis. Therefore, an experiment was conducted to confirm that CN-400-4, when applied to the skin, could remain in the epidermis and effectively does not exhibit UV-induced skin damage on an artificial skin membrane (Franz Cell Membrane, FCM). When CN-400-4 was applied to artificial skin, it was incubated for 4 hours on FCM under 30 minutes of light irradiation, washed three times with PBS, and then H&E staining was performed to confirm the degree of skin damage, the result of confirming is shown in FIG. 12. As confirmed in FIG. 12, CN-400-4 remained in the stratum corneum on the skin surface, so it was confirmed that it protected the skin without damage even in the case of UV irradiation, as confirmed in the right figure, however in the control group (left figure), it was confirmed that the skin damage caused by UV irradiation was tearing of the stratum corneum and damage to the epidermis. Therefore, CN-400-4 remained in the stratum corneum, effectively protecting against skin damage caused by UV, and it was confirmed that the stratum corneum and epidermis were not damaged when applied.

Figure 13:
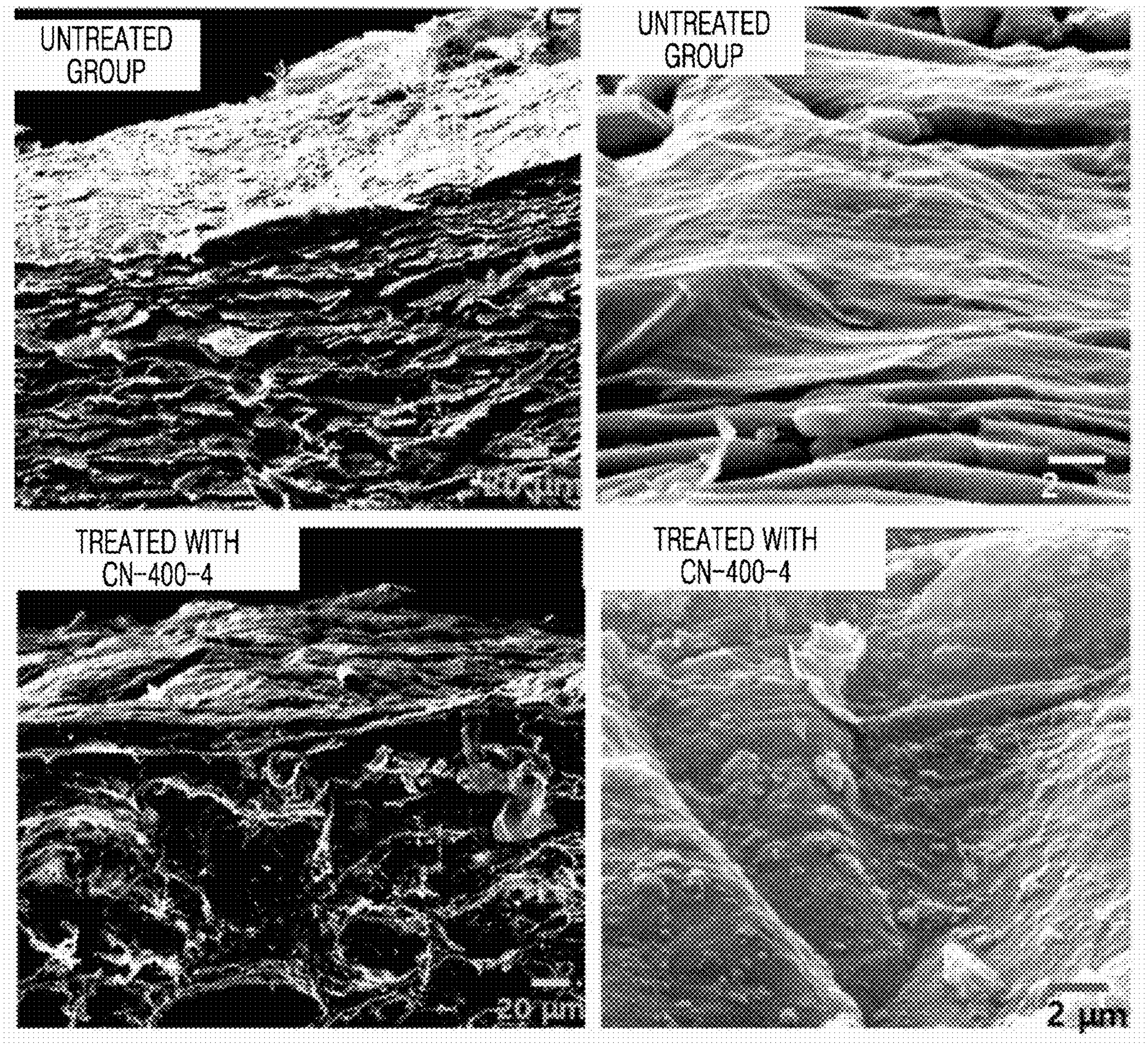
FIG. 13 shows the result of confirming the cross-section of FCM by SEM to observe the morphology of the skin surface of the CN-400-4 applied case and the untreated group, which is a control group.

In addition, to confirm that CN-400-4 effectively remains on the skin surface without penetrating the skin epidermis, the skin surface of FCM was examined by scanning electron microscopy (SEM) to observe the morphology of the skin surface in the case of CN-400-4 application on the skin surface. The CN-400-4 sample was treated with FCM, washed three times with PBS, and the FCM was lyophilized to confirm the SEM, which is shown in FIG. 13. As confirmed in the bottom view of FIG. 13, it was confirmed that CN-400-4 improved the interaction between the stratum corneum indicated by the arrow and CN-400-4, and remained on the outermost surface of the stratum corneum in a sheet structure. In contrast, as confirmed in the upper view of FIG. 13, it was confirmed that unlike the CN-400-4 treated group, the surface of the untreated FCM showed a smooth skin without any uneven pattern on the surface.

7.4 Results of Skin Irritation (Patch) Tests to Confirm Stability as UV-Blocking Agent Conducted at SEMYUNG University Bio Industry Clinical Testing Center under IRB approval. Certified for use on human skin by the SEMYUNG University Bio Industry Clinical Testing Center. It was confirmed after 30 minutes, 24 hours, and 48 hours, all 30 subjects showed no skin irritation. The experiment was conducted and certified according to the standards of the International Contact Dermatitis Research Group (ICDRG). A patch test was conducted to confirm that CN-400-4 did not cause irritation even in actual skin stimulation. CN-400-4 patches were produced for 30 subjects, and the response of the CN-400-4 patches on the skin of the subject was checked three times after 30 minutes, 24 hours, and 48 hours, and is shown in FIG. 14. As confirmed in FIG. 14, the CN-400-4 patch was 100% negative for all 30 subjects, confirming no skin irritation. Therefore, it was confirmed that CN-400-4 is non-toxic, non-skin irritating, and stable enough to be used effectively on human skin.

While the above has described in detail certain aspects of the present disclosure, it will be apparent to one of ordinary skill in the art that such specific descriptions are merely preferred embodiments and the scope of the present invention is not limited thereto. Therefore, the substantive scope of the present disclosure is defined by the appended claims and their equivalents.

The invention claimed is:

1. A crystal form of polymeric carbon nitride (PCN), selected from the group consisting of crystal forms A to G having the following X-ray powder diffraction patterns as measured using CuKα radiation, wherein the polymeric carbon nitride comprises repeating units represented by the following Formula 1, and wherein the X-ray powder diffraction pattern of the crystal form A comprises peaks at one or more diffraction angles selected from the group consisting of $2\theta=10.7656\pm0.2°$, $19.8006\pm0.2°$, and $29.7456\pm0.2°$, the X-ray powder diffraction pattern of the crystal form B comprises peaks at one or more diffraction angles selected from the group consisting of $2\theta=10.7396\pm0.2°$ and $29.7456\pm0.2°$, the X-ray powder diffraction pattern of the crystal form C comprises peaks at one or more diffraction angles selected from the group consisting of $2\theta=10.7006\pm0.2°$, $22.1406\pm0.2°$, and $27.8606\pm0.2°$, the X-ray powder diffraction pattern of the crystal form D comprises peaks at one or more diffraction angles selected from the group consisting of $2\theta=10.6356\pm0.2°$ and $27.8216\pm0.2°$, the X-ray powder diffraction pattern of the crystal form E comprises peaks at one or more diffraction angles selected from the group consisting of $2\theta=10.7266\pm0.2°$ and $27.5096\pm0.2°$, the X-ray powder diffraction pattern of the crystal form F comprises a peak at a diffraction angle of $2\theta=27.1586\pm0.2°$, and the X-ray powder diffraction pattern of the crystal form G comprises peaks at one or more diffraction angles selected from the group consisting of $2\theta=13.8076\pm0.2°$ and $27.1586\pm0.2°$;

[Formula 1]

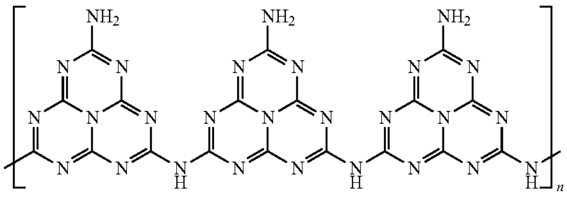

wherein, in Formula 1 above, the n is an integer from 1 to 1,000,000.

2. The crystal form of claim 1, selected from the group consisting of:

the crystal form A of which an infrared (IR) spectrum comprises characteristic absorption peaks at 775±2 $cm^{-1}$, 1417 $cm^{-1}$, 1456 $cm^{-1}$, 1691 $cm^{-1}$, 1730 $cm^{-1}$, 3074 $cm^{-1}$, and 3311 $cm^{-1}$;

the crystal form B of which an IR spectrum comprises characteristic absorption peaks at 777±2 $cm^{-1}$, 1677±2 $cm^{-1}$, 1735±2 $cm^{-1}$, 3085±2 $cm^{-1}$, and 3315±2 $cm^{-1}$;

the crystal form C of which an IR spectrum comprises characteristic absorption peaks at 777±2 $cm^{-1}$, 1467±2 $cm^{-1}$, 1666±2 $cm^{-1}$, 1734±2 $cm^{-1}$, 3120±2 $cm^{-1}$, and 3320±2 $cm^{-1}$;

the crystal form D of which an IR spectrum comprises characteristic absorption peaks at 777±2 $cm^{-1}$, 1465±2 $cm^{-1}$, 1660±2 $cm^{-1}$, 1734±2 $cm^{-1}$, 3085±2 $cm^{-1}$, and 3330±2 $cm^{-1}$;

the crystal form E of which an IR spectrum comprises characteristic absorption peaks at 810±2 $cm^{-1}$, 1270±2 $cm^{-1}$, 1420±2 $cm^{-1}$, 1612±2 $cm^{-1}$, 3105±2 $cm^{-1, and}$ 3330±2 $cm^{-1}$;

the crystal form F of which an IR spectrum comprises characteristic absorption peaks at 810±2 $cm^{-1}$, 1265±2 $cm^{-1}$, 1325±2 $cm^{-1}$, 1417±2 $cm^{-1}$, 1618±2 $cm^{-1}$, and 3230±2 $cm^{-1}$; and the crystal form G of which an IR spectrum comprises characteristic absorption peaks at 810±2 $cm^{-1}$, 1240±2 $cm^{-1}$, 1317±2 $cm^{-1}$, 1410±2 $cm^{-1}$, 1560±2 $cm^{-1}$, 1635±2 $cm^{-1}$, and 3250±2 $cm^{-1}$.

3. The crystal form of claim 1, wherein upon X-ray photoelectron spectroscopy (XPS) analysis, the crystal form has a carbon (C) peak in a range of 280 eV to 290 eV, a nitrogen (N) peak in a range of 390 eV to 400 eV, and an oxygen (O) peak in a range of 530 eV to 540 eV.

4. The crystal form of claim 1, wherein the crystal form absorbs light energy in a wavelength range of 200 nm to 400 nm.

5. The crystal form of claim 1, wherein an average particle diameter of the crystal form is from 1 nm to 10 nm.

6. The crystal form of claim 1, wherein the crystal form does not exhibit cytotoxicity to fibroblasts.

7. The crystal form of claim 1, wherein the crystal form does not generate reactive oxygen species (ROS) when irradiated with UV.

8. A cosmetic composition comprising a polymeric carbon nitride (PCN) comprising repeating units represented by the following Formula 1:

wherein the PCN comprises a crystal form of the PCN selected from the group consisting of crystal forms A to G having the following X-ray powder diffraction patterns as measured using CUKα radiation, wherein the X-ray powder diffraction pattern of the crystal form A comprises peaks at one or more diffraction angles selected from the group consisting of 2θ=10.7656±0.2°, 19.8006±0.2° and 29.7456±0.2°, the X-ray powder diffraction pattern of the crystal form B comprises peaks at one or more diffraction angles selected from the group consisting of 2θ=10.7396±0.2° and 29.7456±0.2°, the X-ray powder diffraction pattern of the crystal form C comprises peaks at one or more diffraction angles selected from the group consisting of 2θ=10.7006±0.2°, 22.1406±0.2°, and 27.8606±0.2°, the X-ray powder diffraction pattern of the crystal form D comprises peaks at one or more diffraction angles selected from the group consisting of 2θ=10.6356±0.2° and 27.8216±0.2°, the X-ray powder diffraction pattern of the crystal form E comprises peaks at one or more diffraction angles selected from the group consisting of 2θ=10.7266±0.2° and 27.5096±0.2°, the X-ray powder diffraction pattern of the crystal form F comprises a peak at a diffraction angle of 26=27.1586±0.2, and the X-ray powder diffraction pattern of the crystal form G comprises peaks at one or more diffraction angles selected from the group consisting of 2θ=13.8076±0.2 and 27.1586±0.2,

[Formula 1]

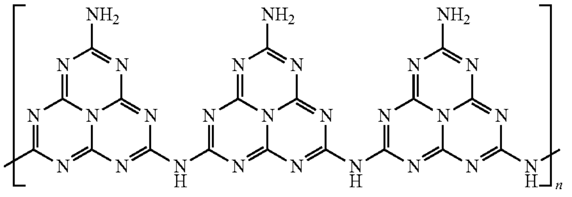

wherein, in Formula 1 above, the n is an integer from 1 to 1,000,000.

9. The cosmetic composition of claim 8, wherein the cosmetic composition is for ultraviolet rays (UV)-blocking.

10. The cosmetic composition of claim 8, wherein the PCN is comprised in an amount of 0.001 wt % to 35 wt %, based on a total weight of the composition.

11. The cosmetic composition of claim 8, wherein the cosmetic composition further comprises one or more selected from the group consisting of an organic UV-blocking agent and an inorganic UV-blocking agent.

12. The cosmetic composition of claim 8, wherein the PCN absorbs light energy in a wavelength range of 200 nm to 400 nm.

13. A composition for UV-blocking comprising a polymeric carbon nitride (PCN) comprising repeating units represented by the following Formula 1:

wherein the PCN comprises a crystal form of the PCN selected from the group consisting of crystal forms A to G having the following X-ray powder diffraction patterns as measured using CUKα radiation, wherein the X-ray powder diffraction pattern of the crystal form A comprises peaks at one or more diffraction angles selected from the group consisting of 2θ=10.7656±0.2°, 19.8006±0.2° and 29.7456±0.2°, the X-ray powder diffraction pattern of the crystal form B comprises peaks at one or more diffraction angles selected from the group consisting of 2θ=10.7396±0.2° and 29.7456±0.2°, the X-ray powder diffraction pattern of the crystal form C comprises peaks at one or more diffraction angles selected from the group consisting of 2θ=10.7006±0.2°, 22.1406±0.2°, and 27.8606±0.2°, the X-ray powder diffraction pattern of the crystal form D comprises peaks at one or more diffraction angles selected from the group consisting of 2θ=10.6356±0.2° and 27.8216±0.2°, the X-ray powder diffraction pattern of the crystal form E comprises peaks at one or more diffraction angles selected from the group consisting of 2θ=10.7266±0.2° and 27.5096±0.2°, the X-ray powder diffraction pattern of the crystal form F comprises a peak at a diffraction angle of 26=27.1586±0.2, and the X-ray powder diffraction pattern of the crystal form G comprises peaks at one or more diffraction angles selected from the group consisting of 20=13.8076±0.2 and 27.1586±0.2,

[Formula 1]

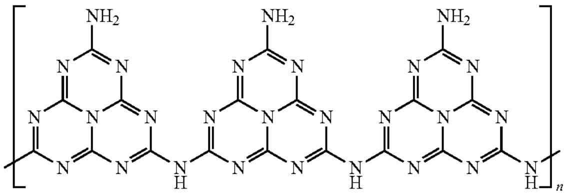

wherein, in Formula 1 above, the n is an integer from 1 to 1,000,000.

* * * * *